(12) United States Patent
Boudreau et al.

(10) Patent No.: US 11,833,313 B2
(45) Date of Patent: Dec. 5, 2023

(54) SYSTEMS AND METHODS FOR MONITORING AND REGULATING PLANT PRODUCTIVITY

(71) Applicant: HORTAU INC., Levis (CA)

(72) Inventors: Jocelyn Boudreau, San Luis Obispo, CA (US); Vincent Pelletier, L'Ancienne-Lorette (CA); Yann Periard Larrivee, Quebec (CA); Rock Chabot, Saint-Lambert-de-Lauzon (CA)

(73) Assignee: HORTAU INC., Levis (CA)

( * ) Notice: Subject to any disclaimer, the term of this patent is extended or adjusted under 35 U.S.C. 154(b) by 100 days.

(21) Appl. No.: 17/268,770

(22) PCT Filed: Aug. 16, 2019

(86) PCT No.: PCT/CA2019/051117
§ 371 (c)(1),
(2) Date: Feb. 16, 2021

(87) PCT Pub. No.: WO2020/034039
PCT Pub. Date: Feb. 20, 2020

(65) Prior Publication Data
US 2021/0235641 A1    Aug. 5, 2021

Related U.S. Application Data

(60) Provisional application No. 62/719,171, filed on Aug. 17, 2018.

(51) Int. Cl.
*A61M 25/00* (2006.01)
*A61M 25/06* (2006.01)
(Continued)

(52) U.S. Cl.
CPC ...... *A61M 25/005* (2013.01); *A61M 25/0662* (2013.01); *A61M 29/00* (2013.01);
(Continued)

(58) Field of Classification Search
CPC ............ A61M 25/0662; A61M 25/005; A61M 29/00; A61M 2025/0186;
(Continued)

(56) References Cited

U.S. PATENT DOCUMENTS

2015/0230417 A1\* 8/2015 Nickerson .............. A01G 25/16
700/284
2018/0235162 A1\* 8/2018 Verma .................. A01G 25/167
2019/0380325 A1\* 12/2019 Bender ................. A01M 99/00

FOREIGN PATENT DOCUMENTS

IN          201811022498       8/2018
WO          2018047726 A1      3/2018
(Continued)

*Primary Examiner* — Chad G Erdman
(74) *Attorney, Agent, or Firm* — BCF LLP

(57) ABSTRACT

System for monitoring and regulating plant productivity comprising: a memory for storing instructions; a processor for executing the instructions to cause a method of monitoring and regulating plant productivity to be performed, the method comprising: receiving field data from monitoring sensors; computing, by the at least one processor executing a machine learning algorithm, a predicted value for a variable associated with the production environment condition of a crop field, the machine learning algorithm having been trained based on a training set comprising one or both of (a) the field data from the monitoring sensors, and (b) a generated feature derived from the field data; and determining, based on a threshold associated with the variable, that the predicted value for the variable indicates that an intervention in the crop field is to be initiated; and in response to the determining, causing a controllable device to vary the production environment condition.

20 Claims, 18 Drawing Sheets

(51) Int. Cl.
　　　*A61M 29/00*　　　(2006.01)
　　　*G05B 19/4155*　　(2006.01)
　　　*A61M 25/01*　　　(2006.01)
　　　*A01G 25/16*　　　(2006.01)

(52) U.S. Cl.
　　　CPC ........ *G05B 19/4155* (2013.01); *A01G 25/167* (2013.01); *A61M 2025/0186* (2013.01); *A61M 2025/0681* (2013.01); *A61M 2025/0687* (2013.01); *G05B 2219/2625* (2013.01)

(58) Field of Classification Search
　　　CPC ............. A61M 2025/0681; A61M 2025/0687; A61M 25/0051; A01G 25/167; G05B 19/4155; G05B 2219/2625
　　　See application file for complete search history.

(56) References Cited

FOREIGN PATENT DOCUMENTS

| WO | 2018081853 A1 | 5/2018 | |
|---|---|---|---|
| WO | WO-2018081853 A1 * | 5/2018 | ............. A01G 25/02 |
| WO | 2018107242 A1 | 6/2018 | |

* cited by examiner

SYSTEMS AND METHODS FOR MONITORING AND REGULATING PLANT PRODUCTIVITY

FIELD

Embodiments described herein relate generally to systems and methods for monitoring plant productivity, and more particularly, to systems and methods for facilitating data-driven regulation of plant productivity.

BACKGROUND

Various techniques have been used that attempt to improve plant productivity. In particular, systems and methods that aim to increase crop yield are known. For example, an irrigation system may be controlled to adjust the level of moisture in the soil. As a further example, genetic improvements may be made to plants to increase their resistance to drought or insects.

SUMMARY

The following summary is for illustrative purposes only, and is not intended to limit or constrain the detailed description. The following summary merely presents various described aspects in a simplified form as a prelude to the more detailed description provided below.

According to various aspects, the present technology relates to a system for monitoring and regulating plant productivity. The system is communicatively couplable to a plurality of monitoring sensors deployable in at least one crop field. The system is further communicatively couplable to at least one controllable device that is operable to vary at least one production environment condition of the at least one crop field, wherein the system comprises: at least one memory for storing a plurality of instructions, and; at least one processor for executing the plurality of instructions to cause a method of monitoring and regulating plant productivity to be performed. According to various aspects, the method comprises: receiving field data from the plurality of monitoring sensors, the field data associated with conditions of the at least one crop field sensed over a monitoring period; computing, by the at least one processor executing a machine learning algorithm, a predicted value for at least one variable associated with the at least one production environment condition of the at least one crop field, the machine learning algorithm having been trained based on a training set comprising one or both of (a) the field data from the plurality of monitoring sensors, and (b) at least one generated feature derived from the field data; and determining, based on a threshold associated with the at least one variable, that the predicted value for the at least one variable indicates that an intervention in the at least one crop field is to be initiated; and in response to the determining, causing the at least one controllable device to vary the at least one production environment condition.

The field data may comprise multiple factors relating to plant productivity and having multiple interactions with one another. For example, field data may comprise data relating to soil of the crop field (such as soil water content, osmotic potential, soil nitrate levels, soil temperature), air (such as air temperature, relative humidity, wind speed and direction, atmospheric pressure, leaf wetness, solar radiation, and rainfall), wildlife (such as spore quantification, insect quantification, foraging bee activity), and irrigation water (such as amount of irrigation water, irrigation water temperature, pH, salinity, nitrate content, fertilizer content).

The at least one variable comprises one or more of: soil tension, soil water content, soil temperature, pH, soil nitrate content, soil salinity, irrigation water amount, irrigation water pH, irrigation water temperature, and the like.

In certain embodiments, the machine learning algorithm takes into account simultaneously the interactions between multiple factors of the field data and/or the at least one generated data.

In certain embodiments, the thresholds associated with the at least one variable are dynamically adjusted, in real-time, in order to improve, optimize or maintain the plant productivity.

According to other aspects, the system is arranged to receive the field data from other sources, such as another processor.

In accordance with at least one embodiment, the method further comprises training the machine learning algorithm based on the training set.

In accordance with at least one embodiment, the method further comprises receiving data of at least one external data type, and the training set further comprises at least a subset of the data of the at least one external data type.

In accordance with at least one embodiment, the training set further comprises data of at least one external data type selected from the following group: data from crop fields other than the at least one crop field, satellite data, drone data, environmental data, weather data, stock price data, resource cost data, resource availability data, and economic data.

In accordance with at least one embodiment, the method further comprises storing data of the training set in at least one multivariate matrix.

In accordance with at least one embodiment, the method further comprises adjusting, by the at least one processor executing the machine learning algorithm, the threshold associated with the at least one variable prior to determining that the predicted value indicates that an intervention in the at least one crop field is to be initiated.

In accordance with at least one embodiment, at least some acts of the method are repeated for at least one subsequent iteration, such that for each subsequent iteration, at the receiving, the field data is associated with conditions of the at least one crop field over a respective subsequent monitoring period.

In accordance with at least one embodiment, the causing the at least one controllable device to vary the at least one production environment condition is performed automatically in response to the determining.

In accordance with at least one embodiment, the method further comprises outputting an alert that intervention in the at least one crop field is desirable, and receiving user confirmation in response to the alert prior to causing the at least one controllable device to vary the at least one production environment condition.

In accordance with at least one embodiment, the method further comprises generating an intervention schedule for permitting a manual assessment of whether intervention in the at least crop field is desirable.

In accordance with at least one embodiment, the method further comprises generating at least one performance assessment report for permitting a manual assessment of crop field performance of the at least one crop field over the monitoring period.

In accordance with at least one embodiment, the determining that the predicted value for the at least one variable indicates that intervention in the at least one crop field is to be initiated comprises: evaluating one or more values for the at least one variable that optimizes plant productivity based on at least one output parameter.

In accordance with at least one embodiment, the at least one output parameter comprises one or more of the output parameters selected from the following group: crop yield, profitability, use of water, use of energy, leaching of fertilizers, and greenhouse gas emissions.

In accordance with at least one embodiment, the at least one output parameter comprises a plurality of output parameters, wherein the method further comprises prioritizing the plurality of output parameters, and wherein the evaluating one or more values for the at least one variable that optimizes plant productivity is based on the plurality of output parameters having been prioritized.

In accordance with at least one embodiment, the method further comprises standardizing the field data, wherein the standardizing comprises aligning the field data in at least one of a spatial dimension and a temporal dimension, and wherein the predicted value for the at least one variable comprises at least one of a spatial component and a temporal component.

In accordance with at least one embodiment, the at least one generated feature derived from the field data comprises a plurality of elements computed from a decomposition of at least one time series associated with the field data.

In accordance with at least one embodiment, the causing the at least one controllable device to vary the at least one production environment condition comprises initiating a change, in the at least one crop field, in at least one of the following elements selected from the following group: water, energy, nitrogen, other elements, chemical inputs. In certain embodiments, chemical inputs comprise pesticides.

From other aspects, there is provided a computing device comprising at least one device processor and at least one device memory, the at least one device processor for initiating performance of the method of monitoring and regulating plant productivity by the at least one processor of the above system, wherein one or more acts of the method are performed on one or more networked devices communicatively coupled to the computing device via at least one network connection.

From yet further aspects, there is provided a method of monitoring and regulating plant productivity comprising: receiving field data from a plurality of monitoring sensors, the field data associated with conditions of the at least one crop field sensed over a monitoring period; computing, by the at least one processor executing a machine learning algorithm, a predicted value for at least one variable associated with the at least one production environment condition of the at least one crop field, the machine learning algorithm having been trained based on a training set comprising one or both of (a) the field data from the plurality of monitoring sensors, and (b) at least one generated feature derived from the field data; and determining, based on a threshold associated with the at least one variable, that the predicted value for the at least one variable indicates that an intervention in the at least one crop field is to be initiated; and in response to the determining, causing at least one controllable device to vary the at least one production environment condition.

From further aspects, there is provided a method of monitoring and regulating plant productivity comprising: computing, by the at least one processor executing a machine learning algorithm, a predicted value for at least one variable associated with the at least one production environment condition of at least one crop field, the machine learning algorithm having been trained based on a training set comprising one or both of (a) field data from a plurality of monitoring sensors, the field data associated with conditions of the at least one crop field sensed over a monitoring period, and (b) at least one generated feature derived from the field data; and determining, based on a threshold associated with the at least one variable, that the predicted value for the at least one variable indicates that an intervention in the at least one crop field is to be initiated; and in response to the determining, causing at least one controllable device to vary the at least one production environment condition.

In accordance with at least one embodiment, the method further comprises: training the machine learning algorithm based on the training set.

In accordance with at least one embodiment, the method further comprises: receiving data of at least one external data type, and wherein the training set further comprises at least a subset of the data of the at least one external data type.

In accordance with at least one embodiment, the method further comprises: receiving the field data from a plurality of monitoring sensors.

In accordance with at least one embodiment, wherein the training set further comprises data of at least one external data type selected from the following group: data from crop fields other than the at least one crop field, satellite data, drone data, environmental data, weather data, stock price data, resource cost data, resource availability data, and economic data.

In accordance with at least one embodiment, the method further comprises: storing data of the training set in at least one multivariate matrix.

In accordance with at least one embodiment, the method further comprises: adjusting, by the at least one processor executing the machine learning algorithm, the threshold associated with the at least one variable prior to determining that the predicted value indicates that an intervention in the at least one crop field is to be initiated.

In accordance with at least one embodiment, at least some acts of the method are repeated for at least one subsequent iteration, such that for each subsequent iteration, at the receiving, the field data is associated with conditions of the at least one crop field over a respective subsequent monitoring period.

In accordance with at least one embodiment, the causing the at least one controllable device to vary the at least one production environment condition is performed automatically in response to the determining.

In accordance with at least one embodiment, the method further comprises: further comprising: outputting an alert that intervention in the at least one crop field is desirable, and receiving user confirmation in response to the alert prior to causing the at least one controllable device to vary the at least one production environment condition.

In accordance with at least one embodiment, the method further comprises: generating an intervention schedule for permitting a manual assessment of whether intervention in the at least crop field is desirable.

In accordance with at least one embodiment, the method further comprises: generating at least one performance assessment report for permitting a manual assessment of crop field performance of the at least one crop field over the monitoring period.

In accordance with at least one embodiment, the determining that the predicted value for the at least one variable indicates that intervention in the at least one crop field is to be initiated comprises: evaluating one or more values for the at least one variable that optimizes plant productivity based on at least one output parameter.

In accordance with at least one embodiment, the at least one output parameter comprises one or more of the output parameters selected from the following group: crop yield, profitability, use of water, use of energy, leaching of fertilizers, and greenhouse gas emissions.

In accordance with at least one embodiment, the at least one output parameter comprises a plurality of output parameters, and wherein the method further comprises: prioritizing the plurality of output parameters, and wherein the evaluating one or more values for the at least one variable that optimizes plant productivity is based on the plurality of output parameters having been prioritized.

In accordance with at least one embodiment, the method further comprises: standardizing the field data, wherein the standardizing comprises aligning the field data in at least one of a spatial dimension and a temporal dimension, and wherein the predicted value for the at least one variable comprises at least one of a spatial component and a temporal component.

In accordance with at least one embodiment, the at least one generated feature derived from the field data comprises a plurality of elements computed from a decomposition of at least one time series associated with the field data.

In accordance with at least one embodiment, the causing the at least one controllable device to vary the at least one production environment condition comprises initiating a change, in the at least one crop field, in at least one of the following elements selected from the following group: water, energy, nitrogen, other elements, chemical inputs.

From other aspects, there is provided a non-transitory computer-readable medium storing instructions that, when executed by a computer comprising at least one processor and at least one memory, cause the at least one processor to perform the method as described above.

From yet further aspects, there is provided a system for monitoring and regulating plant productivity, wherein the system is communicatively couplable to a plurality of monitoring sensors deployable in at least one crop field, wherein the system is further communicatively couplable to at least one controllable device that is operable to vary at least one production environment condition of the at least one crop field, the system configured to cause the at least one production environment condition to be varied based on comparing at least one measure of the at least one production environment condition and at least one automatically adjusted thresholds for the at least one measure.

According to various aspects, the present technology also relates to a computing device comprising at least one device processor and at least one device memory. The device processor initiates performance of a method of monitoring and regulating plant productivity by the processor of the system in accordance with at least one embodiment described herein, wherein one or more acts of the method are performed on one or more networked devices communicatively coupled to the computing device via at least one network connection.

In certain aspects and embodiments of the above, an automated or semi-automated method is possible. The method can be performed in real-time. No prior physical characterization of the soil is required in certain embodiments. Advantageously, in certain embodiments, many production environment conditions of the crop field are taken into account to determine whether an intervention is necessary. Inter-relationships between the production environment conditions are accounted for so that not only parameters directly related to the at least one variable are taken into account, but also secondary parameters with indirect effect.

The summary here is not an exhaustive listing of the novel features described herein, and is not limiting of the claims. These and other features are described in greater detail below.

BRIEF DESCRIPTION OF THE DRAWINGS

These and other features, aspects, and advantages of the present disclosure will become better understood with regard to the following description, claims, and drawings. The present disclosure is illustrated by way of example, and not limited by, the accompanying figures in which like numerals indicate similar elements.

Figure 1:
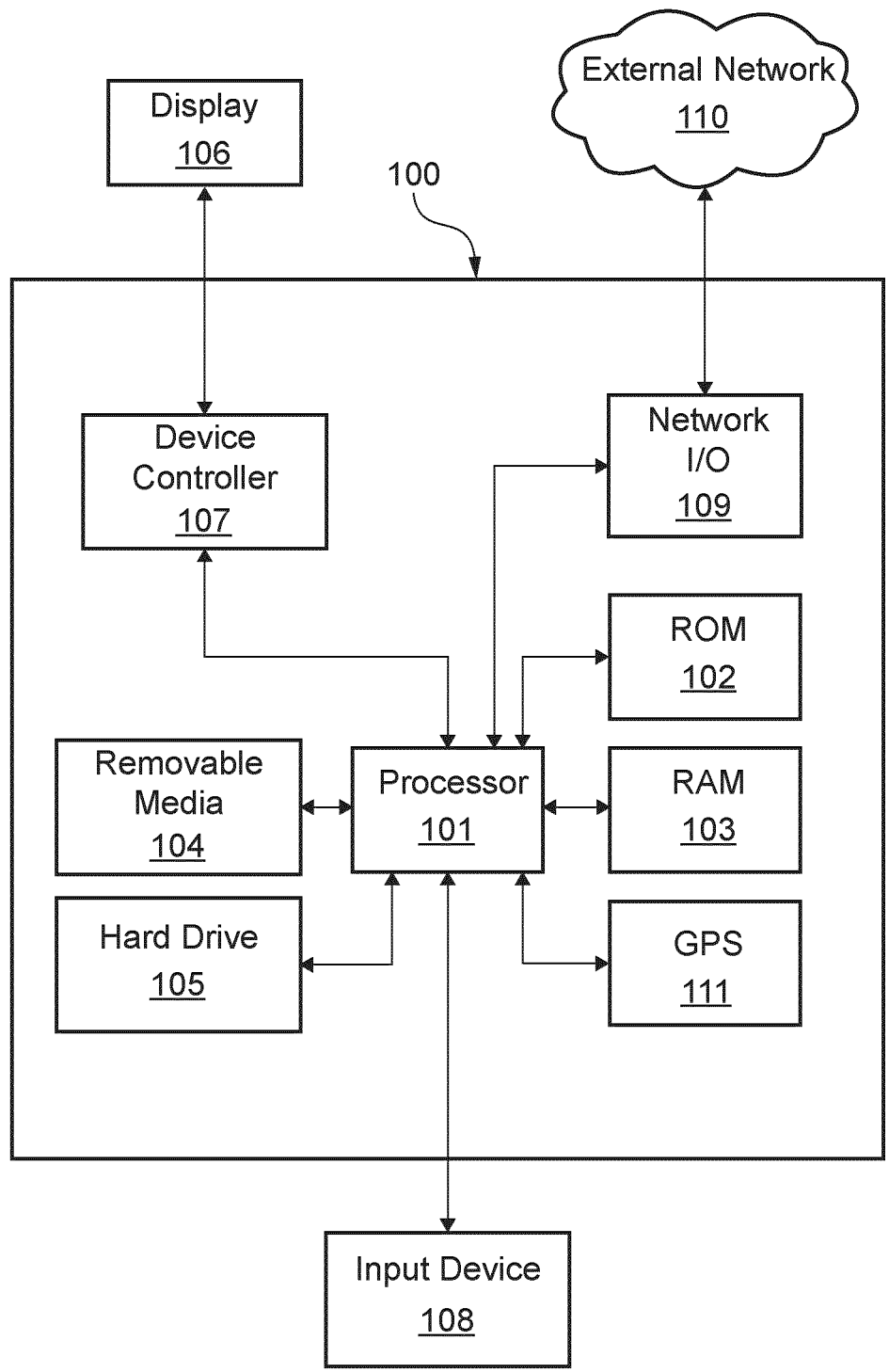
FIG. 1 shows an example computing system that may be used to implement any of the methods described herein.

It is to be expressly understood that the description and drawings are only for the purpose of illustrating certain embodiments of the present technology and are an aid for understanding. They are not intended to be a definition of the limits of the technology.

DETAILED DESCRIPTION

In the following description of various illustrative embodiments, reference is made to the accompanying drawings, which form a part hereof, and in which are shown, by way of illustration, various embodiments in which aspects of the disclosure may be practiced. It is to be understood that other embodiments may be utilized, and structural or functional modifications may be made, without departing from the scope of the present disclosure.

As used herein, the singular form "a," "an" and "the" include plural referents unless the context clearly dictates otherwise.

The expression "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

At least some conventional methods for increasing crop yields focus on detecting and correcting for merely one or a small number of sources of stress. However, crop yield losses are often caused by numerous stresses to which crops are subject, during their growth or during dormant and post-harvest periods. Focusing primarily or solely on, for example, the modification of irrigation practices can fail to account for interactive effects between soil moisture levels and other factors that potentially affect plant productivity.

In a broad aspect, systems and methods capable of accounting for a multitude of factors that may affect plant productivity are disclosed herein. In respect of at least one example embodiment, not only do the systems and methods facilitate the monitoring of field conditions through the collection of data obtained from field sensors, but they are also capable of regulating plant productivity in an autonomous manner by directly controlling devices that can vary those conditions that are expected to impact plant productivity. Controlled devices may act to, for example, minimize water stress, heat stress, damage from frost, soil nutrient deficiencies, damage due to disease or pests, and so on.

By way of illustration, at least some embodiments of a system and method for monitoring and regulating plant productivity may evaluate the interactions between sensor data (historic and/or real-time), quantities or features derived from the sensor data, data from a wide variety of external sources, and varying combinations thereof. In some embodiments, productivity, efficiency, and/or profitability factors may also be evaluated.

Moreover, the analysis performed may comprise applications of learning algorithms, including predictive machine learning algorithms, the performance of which is expected to improve over time as data associated with responses to corrective actions initiated by the system are fed back to the system. Accordingly, devices may be controlled not only to reduce detected stress levels but also to initiate preventative measures in order to address potential increases in stresses determined to be likely in the absence of intervention, or to otherwise enhance protections against anticipated conditions that may adversely affect growth. Thresholds that may define when preventative and/or corrective actions are to be taken can be dynamically adjusted. This may lead to an overall reduction in the level of stresses experienced by a crop, which in turn may result in a marked improvement of crop health and/or crop yields. The system may also facilitate optimization of one or more other parameters of interest, including crop quality, size (or grade), root development (e.g. for young trees or vines), etc.

These and other example aspects and embodiments will be apparent from the description that follows.

FIG. 1 shows an example computing system 100 that can be used to implement any of the various computing devices discussed herein. In one example implementation, a server is employed that may comprise some or all of the components of system 100, typically in addition to other components (not shown for brevity) as will be appreciated by persons skilled in the art. Functions of a server or other computing device may be executed on varying devices, including but not limited to: a personal computer, a notebook computer, a tablet computer, and/or a mobile communications device, as examples.

Computing system 100 may include one or more processors, collectively denoted as processor 101 in FIG. 1. Processor 101 may execute instructions of a computer program to perform any of the features described herein. Processor 101 may comprise, for example, one or more central processing units (CPUs), one or more graphic processing units (GPUs), and/or one or more tensor processing units (TPUs). The instructions may be stored in any type of computer-readable medium or memory, to configure the operation of processor 101. For example, instructions may be stored in one or more of read-only memory (ROM) 102, random access memory (RAM) 103, removable media 104, such as a Universal Serial Bus (USB) drive, compact disk (CD) or digital versatile disk (DVD), floppy disk drive, flash memory, or any other desired storage medium. Instructions may also be stored in an attached, or internal, hard drive 105. Computing system 100 may include one or more output devices, such as one or more displays, collectively denoted as display 106 in FIG. 1, and may include one or more output device controllers 107, such as a video processor. There may also be one or more user input devices 108, such as a keyboard, mouse, touch screen, microphone, etc. Input devices 108 may also comprise, or be communicatively coupled to, devices that provider sensor data, such an accelerometer, device temperature sensor, and so on. Computing system 100 may also include one or more network interfaces, such as a network input/output (I/O) circuit 109, for example, a network card, to communicate with an external network 110 and/or other networked devices. Network I/O circuit 109 may be a wired interface, wireless interface, or a combination of the two. Computing system 100 may comprise a location-detecting device, such as a global positioning system (GPS) microprocessor 111, which can be configured to receive and process global positioning signals and determine, with possible assistance from an external server and antenna, a geographic position of computing system 100.

FIG. 1 illustrates a hardware configuration of a computing device in an example implementation of computing system 100, but it should be understood that some or all of the illustrated components may be implemented as software. In some implementations, hardware and software elements may co-exist in a common physical platform. Additionally, modifications may be made to add, remove, combine, or distribute components of computing system 100.

One or more aspects of the disclosure may be embodied in computer-usable data or computer-executable instructions, such as in one or more program modules, executed by one or more computing devices and/or other devices. Generally, program modules include routines, programs, objects, components, data structures, and other elements that perform particular tasks or implement particular abstract data types when executed by a processor in a computing device or other device. The computer-executable instructions may be stored on one or more computer-readable media including but not limited to: a hard disk, an optical disk, solid state memory, RAM, ROM, removable storage media, flash memory, and so on. In various embodiments, the functionality of the program modules may be combined into or distributed among one or more modules residing on one or more devices; the functionality may also be embodied in whole or in part in firmware or hardware equivalents, including but not limited to: integrated circuits, field programmable gate arrays (FPGA), and so on.

Figure 2:
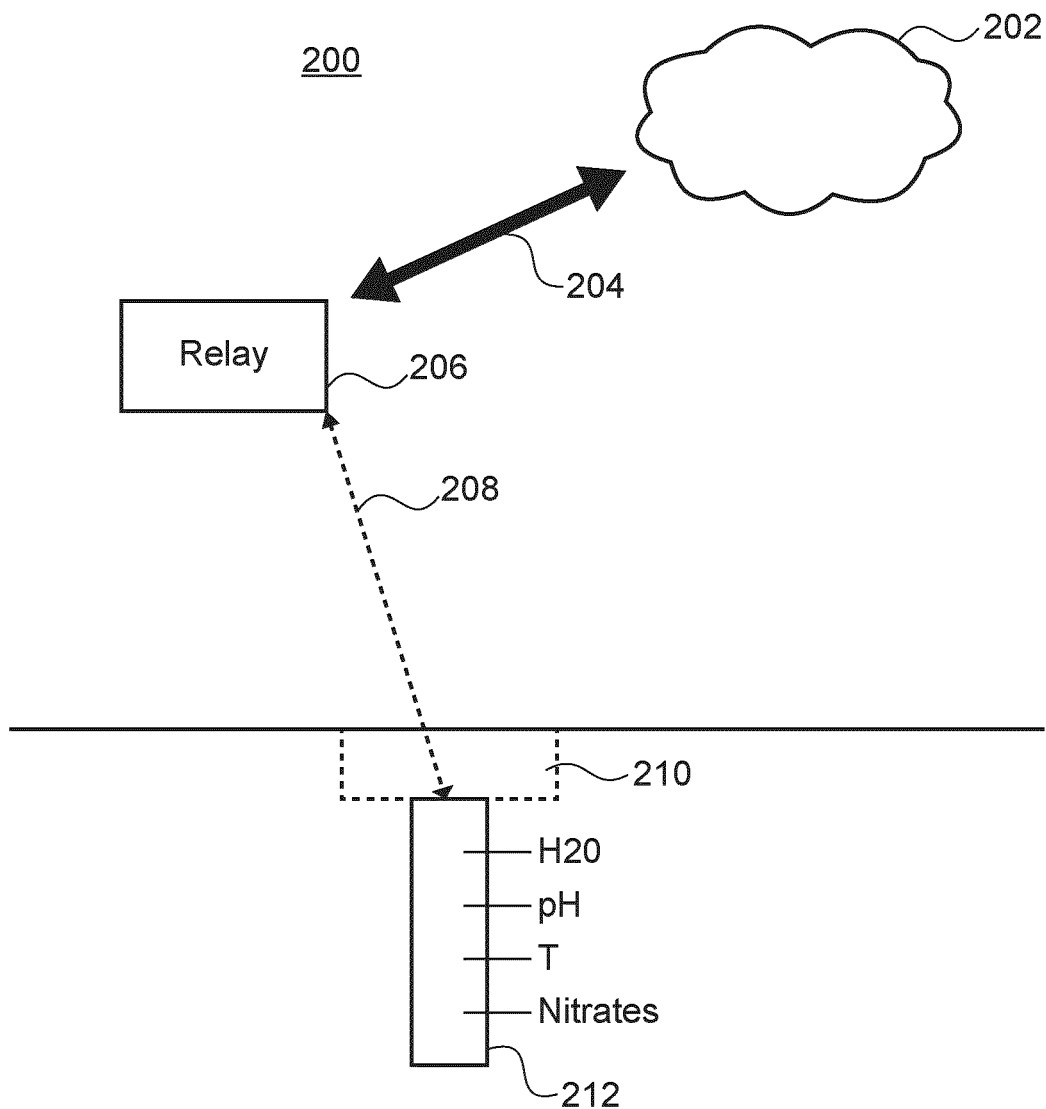
FIG. 2 shows an example sensor device.

FIG. 2 shows an example sensor device 200 that may be used in one or more embodiments described herein. Sensor device 200 may comprise a relay 206 and a sensor 212. Sensor device 200 may communicate with a communication network 202, which may be part of or coupled to network 110 (FIG. 1). The communication network 202 may be connected to or communicating with one or more data processing systems (e.g., computing system 100 of FIG. 1), and each data processing system may manage some or all data received from sensor device 200. Data received from sensor device 200 may be stored in a database (not explicitly shown in FIG. 2).

Relay 206 (which may be referred to as a "gateway") may establish a communication connection 208 between sensor 212 and relay 206. Relay 206 may establish a communication connection 204 between relay 206 and communication network 202, or a system accessed using the communication network 202, such as a data processing system. In certain instances of operation, both communication connection 204 and communication connection 208 may be initialized and/or active, while in other instances only one of the communication connections may be active, or a greater number of communication connections may be initialized and/or active. In some implementations, communication connections 204 and/or 208 may be wireless, with communications thereon governed by one or more wireless communication protocols. A wireless communication protocol may be used to exchange data between relay 206, which may be installed above ground, and sensor 212, which may be above ground or buried underground. Wired or wireless communications may be used to transmit data through a ground area 210. The wireless communication protocol may use low power consumption. Sensor 212 may communicate with other sensors (e.g., at least one other sensor 212). Data communicated between relay 206, sensor(s) 212, and/or communication network 202 may be encrypted.

Sensor 212 (which may also be referred to as a "field sensor" or "probe") may be self-contained and/or may comprise an electrical power source. Sensor 212 may measure one or more variables associated with soil conditions. Examples of variables that can be measured include, but are not limited to: soil tension, soil water content, soil temperature, pH, soil nitrate content, and soil salinity. Other examples may be identified and described elsewhere in the present disclosure.

Data measured by sensor 212 may be transmitted, through relay 206, to communication network 202. Sensor 212 may be located above ground and/or may be buried at a depth. A depth of sensor 212 may be selected based on a type of variable to be measured. A location and/or depth of sensor 212 may be selected based on whether sensor 212 is to maintain communication link 208 with relay 206. Communications between sensor 212 and communication network 202 may occur without passing through relay 206 or a gateway or the like.

In some implementations, sensor device 200 may measure data continuously and/or in real-time. Moreover, one or more sensor devices 200, or one or more portions of sensor devices 200, may be grouped together to form a sensor station. Depending on the particular implementation, a sensor station may comprise one or more relays, and may connect, directly or indirectly, to one or more data processing systems.

Figure 3:
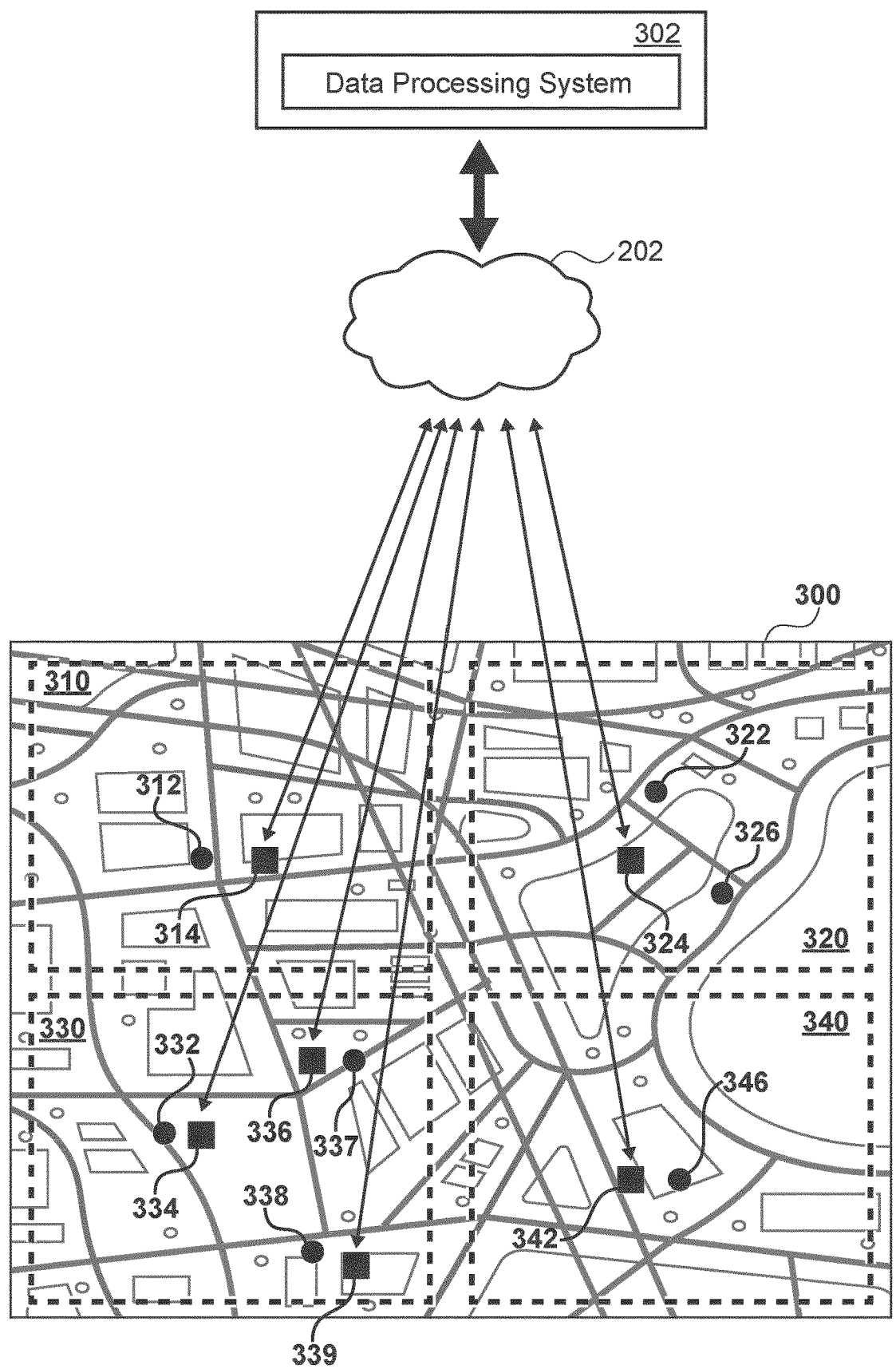
FIG. 3 shows an example implementation in which data is collected from sensor devices.

FIG. 3 shows an example implementation where data is collected from sensor devices. FIG. 3 illustrates multiple sensor devices (e.g. sensor device 200 of FIG. 2) that communicate with a data processing system 302 over a communication network 202. The sensor devices are located in an area comprising four plots of land 310, 320, 330, and 340. Plot 310 comprises a sensor 312 and a relay 314, which form one sensor device. Plot 320 comprises two sensors 322 and 326, and one relay 324. Plot 330 comprises three sensors 332, 337, and 338, and three relays 334, 336, and 339. Plot 340 comprises one sensor 346 and one relay 342.

Sensors 312, 322, 326, 332, 337, 338, and 346 are deployed in plots 310, 320, 330, and 340, and may measure variables, such as variables indicating soil conditions in the plots 310, 320, 330, and 340. Each of sensors 312, 322, 326, 332, 337, 338, and 346 may measure one or more variables associated with the soil conditions of their respective area. Relays 314, 324, 334, 336, 339, and 342 may transmit data using the communication network 202. Data processing system 302 may receive data transmitted by the relays 314, 324, 334, 336, 339, and 342. Data processing system 302 may transmit the received data, analyze the received data, store the received data in a database, and/or perform any other functions with all or a portion of the received data.

Data processing system 302 may receive and/or store various types of data, such as topographical data, soil data, hydrographic data, soil use data, wildlife data, plant data, meteorological data, and/or other types of data. For example, data processing system 302 may receive and/or store visible spectral data and/or non-visible spectral data of the areas 310, 320, 330, and 340. Non-visible spectral data of the area may comprise measurements of wavelengths ranging from ultraviolet to microwaves.

Data measured by the sensor devices and/or managed by data processing system 302 may be used, as described in further detail below, to manage plant productivity.

Figure 4:
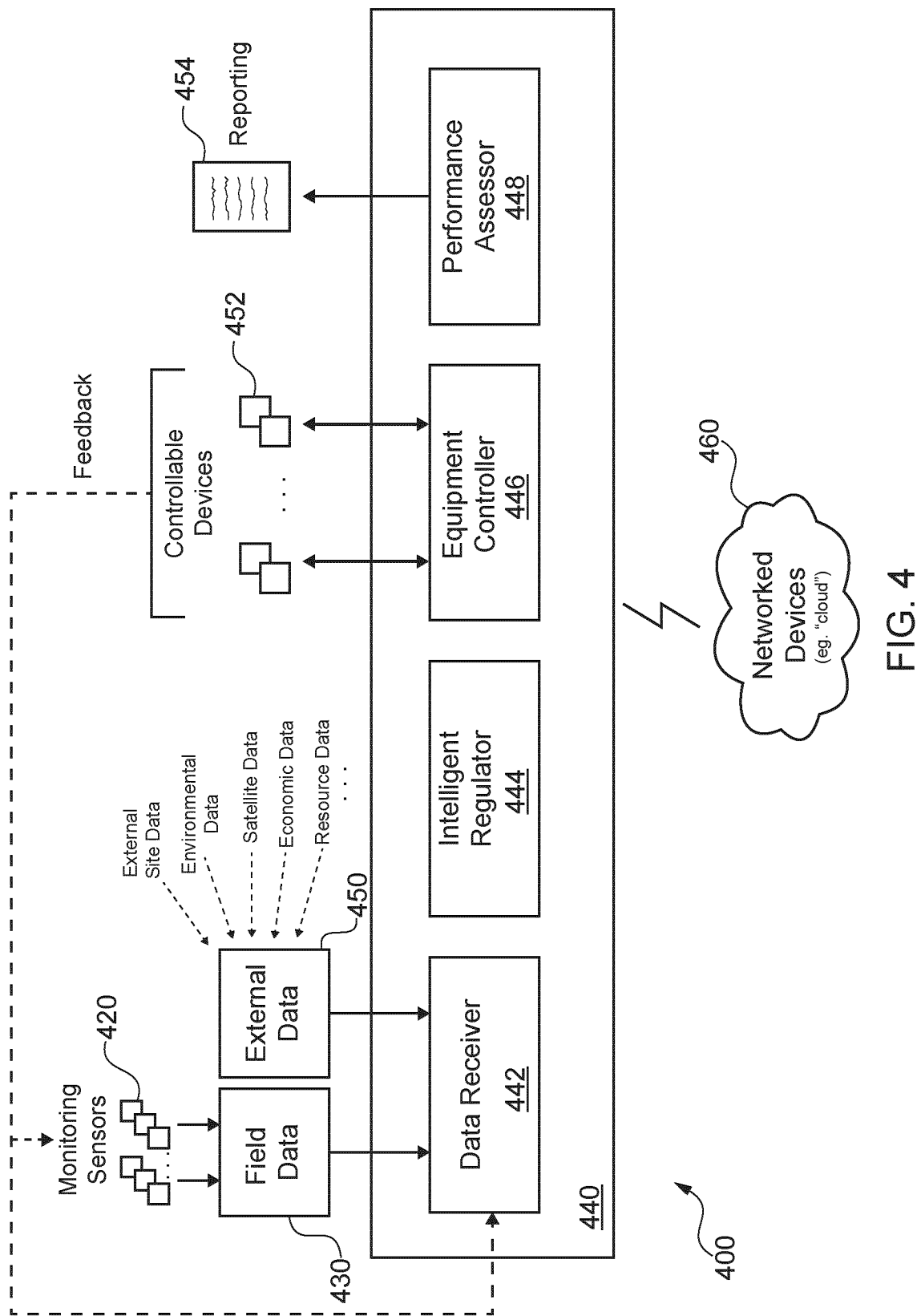
FIG. 4 is a diagram of a system for monitoring and regulating plant productivity according to one or more illustrative aspects of the disclosure.

FIG. 4 is a block diagram illustrating example components of a plant productivity system 400 for monitoring and regulating plant productivity according to one or more illustrative aspects of the disclosure. The system illustrated in FIG. 4 may use sensors, such as real-time sensors. Additionally, system 400 may employ statistical and numerical analysis and/or machine learning techniques to regulate conditions affecting plant productivity. In at least one embodiment, system 400 is operable to recommend changes to current or future operations to optimize plant productivity, or more broadly, to optimize a desired output.

Monitoring sensors 420 may collect field data 430 (also referred to herein generally as sensor data), such as data indicating soil conditions, weather, water quality, or any other data related to factors that may have an impact on plant productivity, potentially in real-time or near-real-time. Monitoring sensors 420 may comprise sensor devices 200 (FIG. 2) described above, or may be any other type of sensor. The field data 430 may comprise multiple factors relating to plant productivity, at least some of the multiple factors having interaction with one another. In some embodiments, the multiple factors have multiple interactions.

Monitoring sensors 420 may each conduct measurements and obtain sensor data relating to one or more variables. For example, monitoring sensors 420 may assess the ability of the soil to provide water and nutrients to crops and more generally detect the presence of favorable or undesirable conditions. Monitoring sensors 420 may be located above or below the ground, in water, on or attached to a structure, or any other location appropriate for measuring variables. Monitoring sensors 420 may be integrated in devices or systems. Any number and type of monitoring sensors 420 may be used in system 400.

Monitoring sensors 420 may be located at different locations of production sites and/or on or integrated within different equipment or machines. Sensor data received by monitoring sensors 420 may reflect changes in field conditions across different locations and/or over time.

By way of illustration, sensor data may be collected in association with one or more soil conditions, including but not limited to: water tension, water content, nitrates content, nutrients content, electrical conductivity, salinity, osmotic potential, water table depth, temperature, aeration level or air content, and pH level. Sensor data may be collected in association with one or more water conditions, including but not limited to: water level, temperature, electrical conductivity, salinity, nitrates content, nutrients content, contaminant levels, and pH level. Sensor data may be collected in association with one or more plant conditions or physiological activity, including but not limited to: canopy temperature, dendrometry data, leaf wetness, leaf temperature, sap flow, stem diameter or stem growth, and xylem potential. Sensor data may be collected in association with one or more biological activities, including but not limited to: pest levels, disease levels, spore levels, weed levels, microbial activity levels, and pollinator activity levels. Sensor data may be collected in association with one or more weather conditions, including but not limited to: temperature, relative humidity, atmospheric pressure, solar radiation, precipitation levels, wind speed, and wind direction. Sensor data may be collected in association with one or more equipment performance measures, including but not limited to: pump pressure levels and oil pressure levels. The various types of data received by monitoring sensors 420 described above are not intended to be limiting; in particular, system 400 may adapt to the monitoring, collection, and analysis of other data that can or may become known to potentially impact plant productivity. In some instances, sensor data received from monitoring sensors 420 may be supplemented by additional data originating from, for example, visual inspection of a given condition in the field.

In at least one embodiment, core processing functions of system 400 may be provided by a computing system 440. In some implementations, computing system 440 may comprise one or more systems or devices, such as that depicted as 100 in FIG. 1. Computing system 440 may comprise a data receiver 442, an intelligent plant productivity regulator 444, an equipment controller 446, and/or a performance assessor 448.

Data receiver 442 may receive data from monitoring sensors 420. For example, data receiver 442 may receive field data 430 from monitoring sensors 420 as it is measured (e.g., in real-time) and/or at various intervals. For example, some monitoring sensors 420 may transmit field data 430 to computing system 440 continuously as data is measured, while other monitoring sensors 420 may transmit field data 430 at preset intervals, such as daily or weekly. Where sensor data is transmitted at certain intervals, the data may reflect conditions at the time of a given transmission and/or conditions over a period of time preceding the given transmission.

In variant embodiments, monitoring system 420 may transmit field data 430 at a time different from a preset interval, as one or more components of computing system 440 determine that certain conditions are met. For example, with respect to air temperature, temperature data may, by default, be transmitted at a preset interval of 30 minutes, but more frequently when frost is imminent. Accordingly, when a certain (e.g., temperature) threshold is met, the transmission frequency may be modified and/or a transmission may be made at moments other than those defined by the preset interval. As a further example, water tension data may be transmitted more frequently than the default interval, during irrigation.

As depicted in FIG. 4, data receiver 442 may also receive and/or collect external data 450. External data may comprise data related to plant productivity that can be collected from sources other than what is directly measured by monitoring sensors 420 deployed at a particular field or site of interest. As examples, external data may not originate from a field sensor, or it may originate from data (e.g., real-time, historical, and/or forecasted) obtained by sensors deployed at one or more sites outside of the site of interest. Accordingly, external data may belong to one or more categories of data including but not limited to: external site data, environmental data, satellite data, resource data, and economic data. The data may be made accessible via a web site, a web service, a database, via an application programming interface (API), a server, a computing system, a device, and/or other data source.

For example, external data 450 may comprise weather data, such as local, regional, and/or predicted weather data. The weather data may comprise wind speed, air humidity, temperature, precipitation, cloud cover index, atmospheric pressure, dew point, evapotranspiration (ET), and/or any other measured or predicted weather data. External data 450 may comprise imaging and spectrography data obtained by various methods, such as fixed cameras, drones, planes, satellites, etc. External data 450 may comprise soil profile data, soil texture or class data, soil granulometry data, soil compaction data, and other data descriptive of certain (e.g., previously measured and/or reported) characteristics and physicochemical, hydraulic, and/or biological properties of the soil at the given site; hydrological data for the site; topographical data for the site; location data for the site, etc. External data 450 may comprise data descriptive of the crop in place, such as species, variety, plantation density, plantation date, physiological stage, harvest objective, irrigation system type, etc.; historical data, such as historical yield data, may also be provided. External data 450 may comprise data related to economic variables, such as stock market prices, input, energy and labor costs, etc. External data 450 may comprise data describing legal and regulatory constraints, such as restrictions on the use of certain resources or inputs. External data 450 may comprise data associated with irrigation constraints, scheduling constraints, cultural practices, etc.

Referring again to FIG. 4, computing system 440 comprises intelligent plant productivity regulator 444, which may analyze field data 430, external data 450, and/or any other collected data. Equipment controller 446 communicates with controllable devices 452. Controllable devices 452, which may comprise equipment and/or machinery, may be instructed, by equipment controller 446, to control the start-up, operation, and/or shutdown of various subsystems such as irrigation, fertigation, and applications of various products, including their availability in tanks. For example, equipment controller 446 may be used to automate the introduction of water and fertilizer into the field, intervene in the prevention of diseases and pests, and/or initiate other interventions such as sowing, plant cutting, tillage, etc. Controllable devices 452 may comprise an actuator controlling a pump (on/off) and/or a solenoid controlling (open/close) a valve for irrigating a field. Any changes resulting from operation of controllable device 452 may subsequently be detected by monitoring sensors 420, thus completing a feedback loop. At least some devices (engines, pumps, fertilizer injectors, filters, etc.) have sensors that provide data that can be transmitted back to components of computing system 440 that may be used as feedback. Where devices are not equipped with such sensors (or when additional feedback is helpful even where such devices are equipped with such sensors), one or more feedback sensors may be employed to assist in determining whether a given device is operating properly. This feedback data may be another source of data that may be used in a machine learning and optimization tasks, as will be discussed below.

Performance assessor 448 may generate one or more status and/or activity reports 454.

At least some of the functions of data receiver 442, intelligent plant production regulator 444, equipment controller 446, and/or performance assessor 448, may be performed on one or more networked devices 460, which may include devices accessible via the Internet (e.g., the "cloud"). Similarly, at least some data utilized by data receiver 442, intelligent plant production regulator 444, equipment controller 446, and/or performance assessor 448 may be stored temporarily and/or permanently on one or more networked devices 460, which may include devices accessible via the Internet (e.g., the "cloud"). Further details of these and other components of computing system 440 will be described herein with reference to Figures that follow.

Figure 5A:
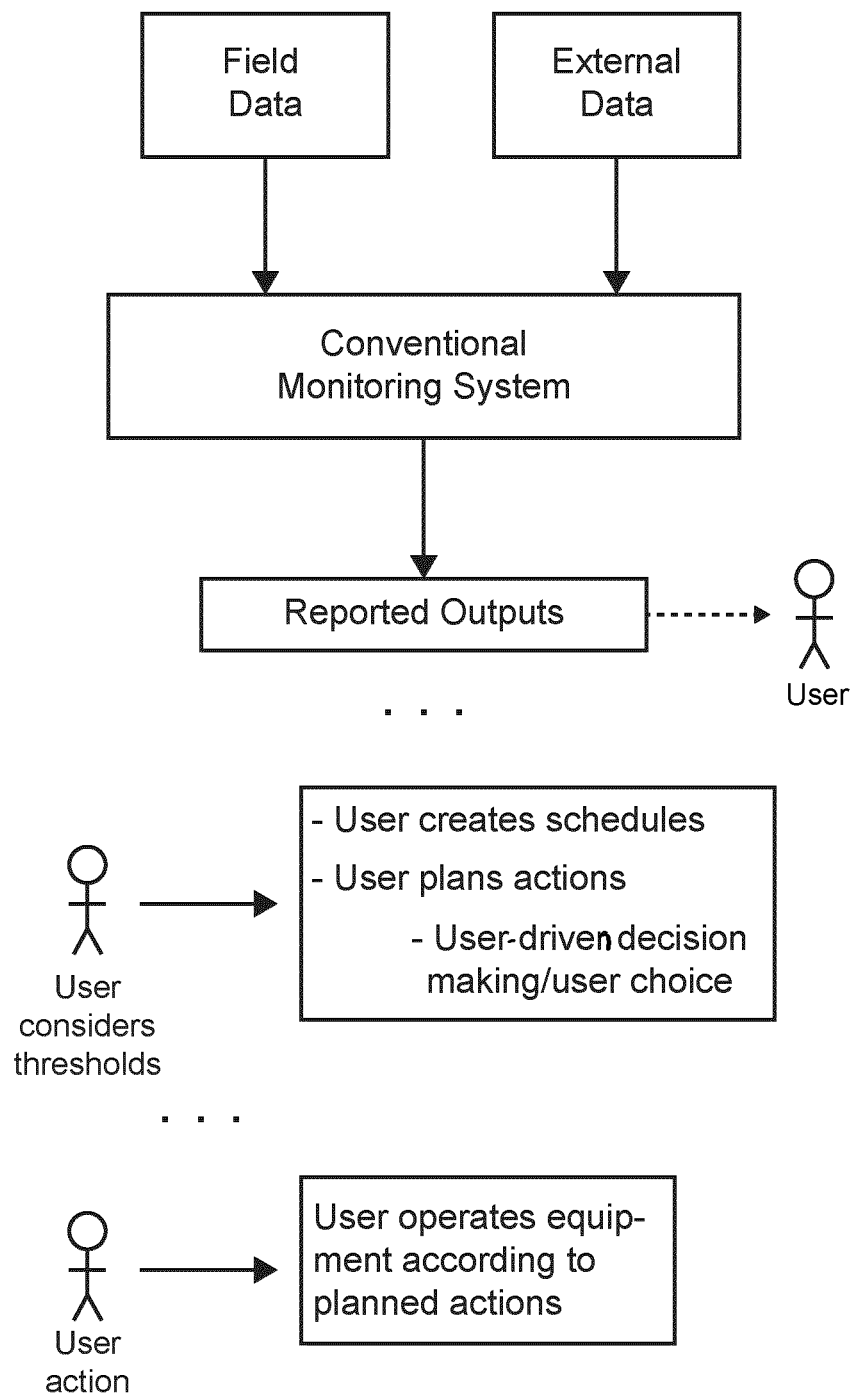
FIGS. 5A and 5B are diagrams that illustrate some differences between certain conventional monitoring systems and features of at least one embodiment of a system for monitoring and regulating plant productivity according to one or more illustrative aspects of the disclosure.
Figure 5B:
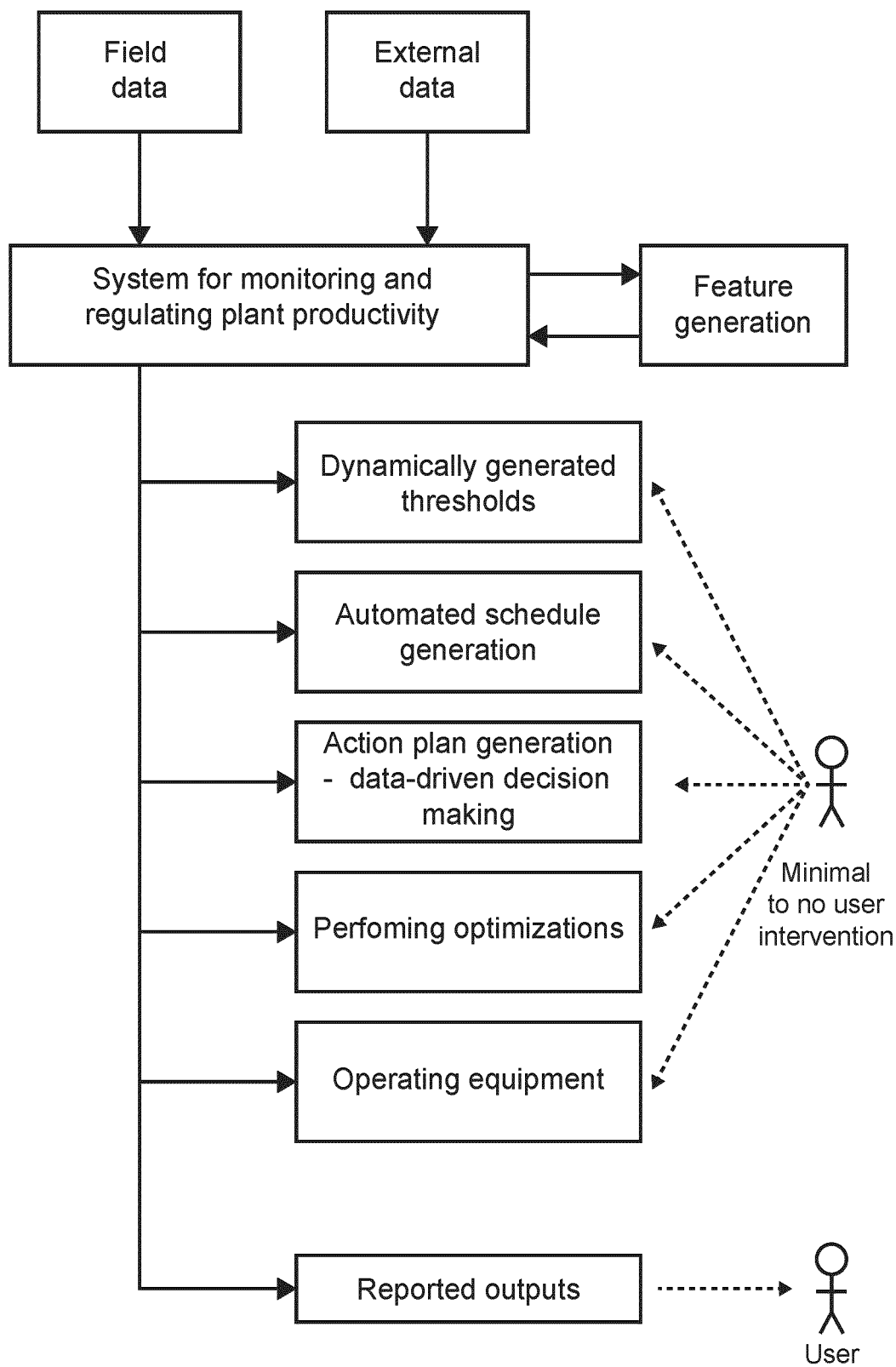

FIG. 5A and FIG. 5B are diagrams that illustrate some differences between certain conventional monitoring systems and features of at least one embodiment of a system for monitoring and regulating plant productivity according to one or more illustrative aspects of the disclosure. In particular, from a broad, user's perspective, the system user is central to the decision-making and intervention process when the conventional monitoring system of FIG. 5A is employed. The user considers the measurements that are received, which may include sensor data, but typically determines thresholds to be applied and makes decisions as to what changes are necessary. The user will generally be responsible for determining appropriate schedules (e.g., operating schedules for equipment) and action plans, and may subsequently operate equipment according to those planned actions. In contrast, again from a broad, user's perspective, in at least one embodiment of the systems and methods described herein, the user may play a more passive role where user intervention is minimized. For example, as shown in FIG. 5B, the system may determine and dynamically adjust thresholds to optimize performance, for a wide variety of supported variables. Depending on implementation and the level of user interaction desired, the system may establish provisional calendars, perform action items, provide alerts and reports to users, and adjust action plans and schedules in response to changing conditions that may affect plant productivity. The user may be provided with varying information (e.g., including real-time, historical, and forecasted data) to aid in determining whether manual intervention, if desired, is required.

Figure 6A:
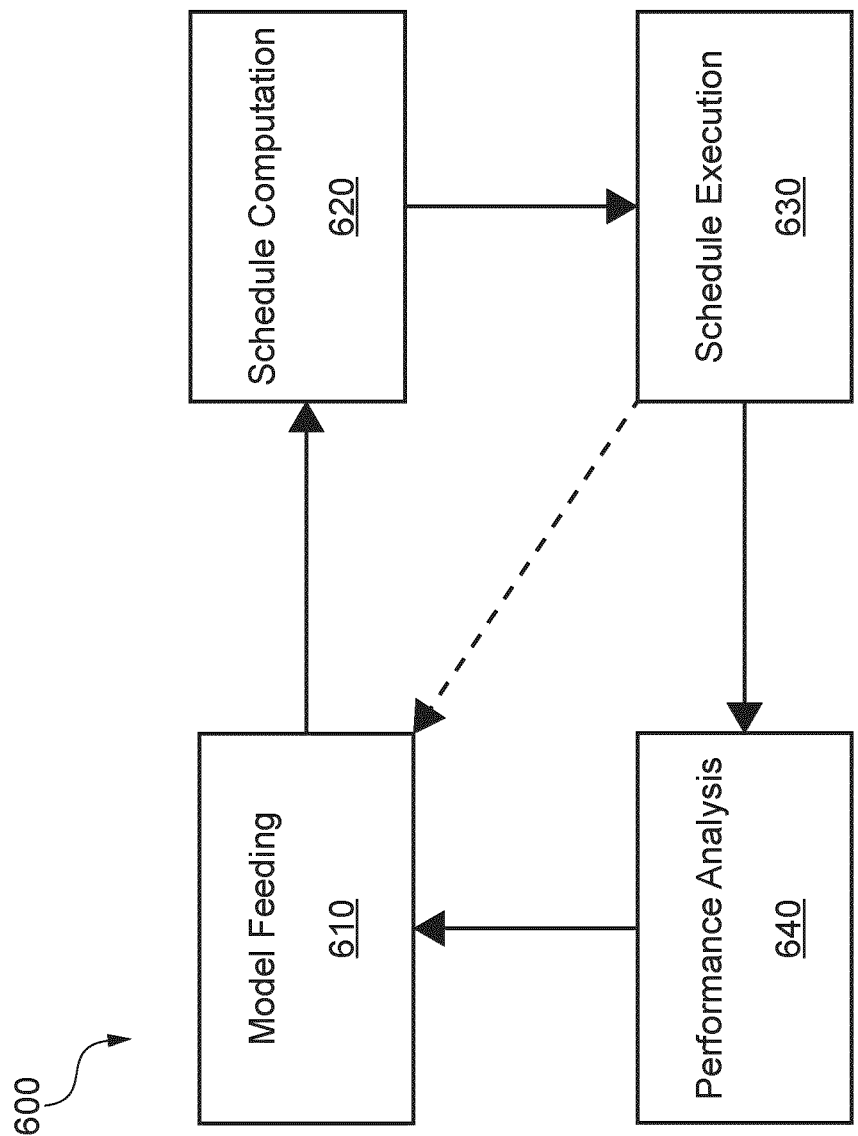
FIGS. 6A through 6C are block diagrams illustrating four example phases of a method for monitoring and regulating plant productivity according to one or more illustrative aspects of the disclosure.
Figure 6B:
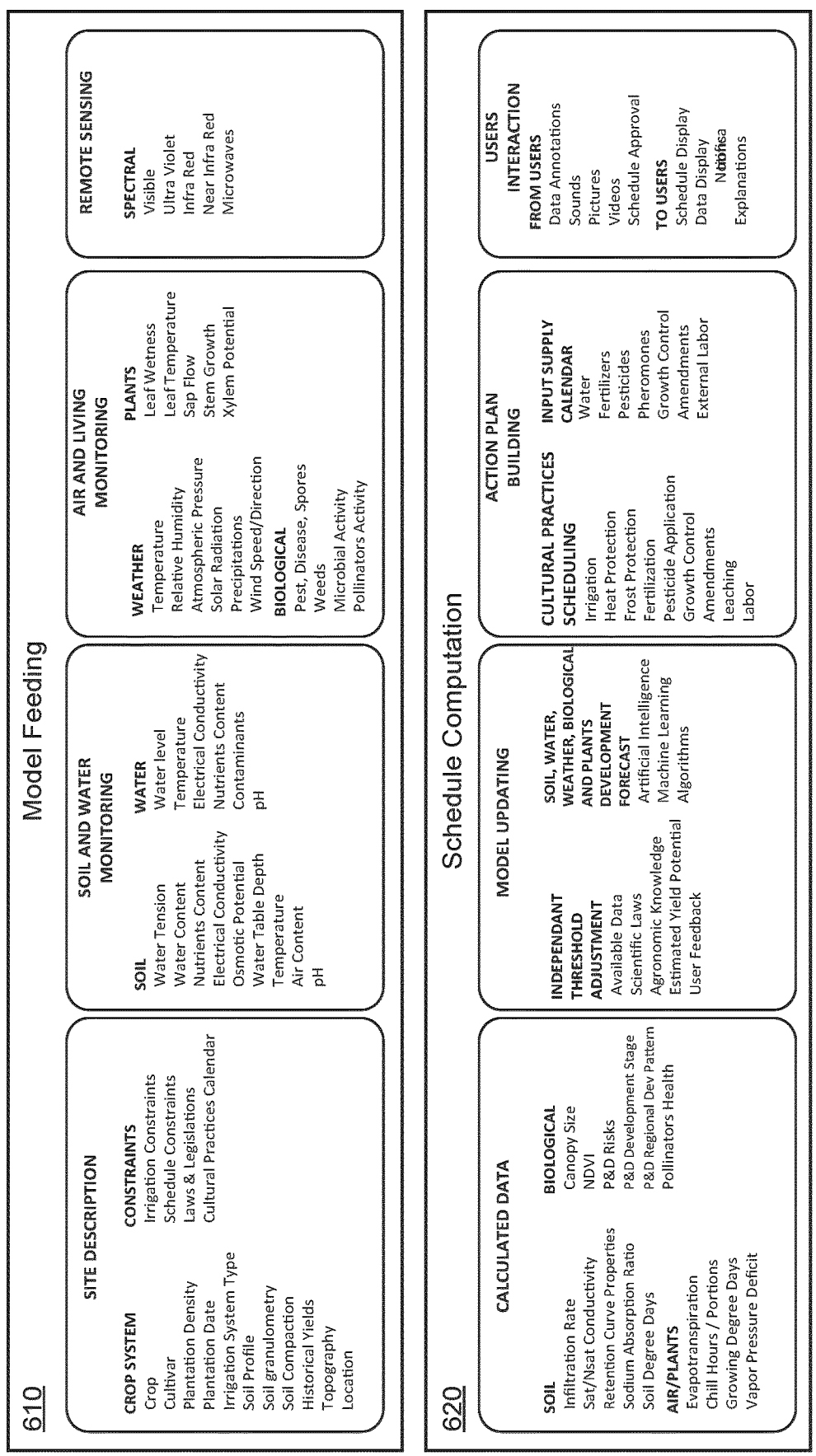
Figure 6C:
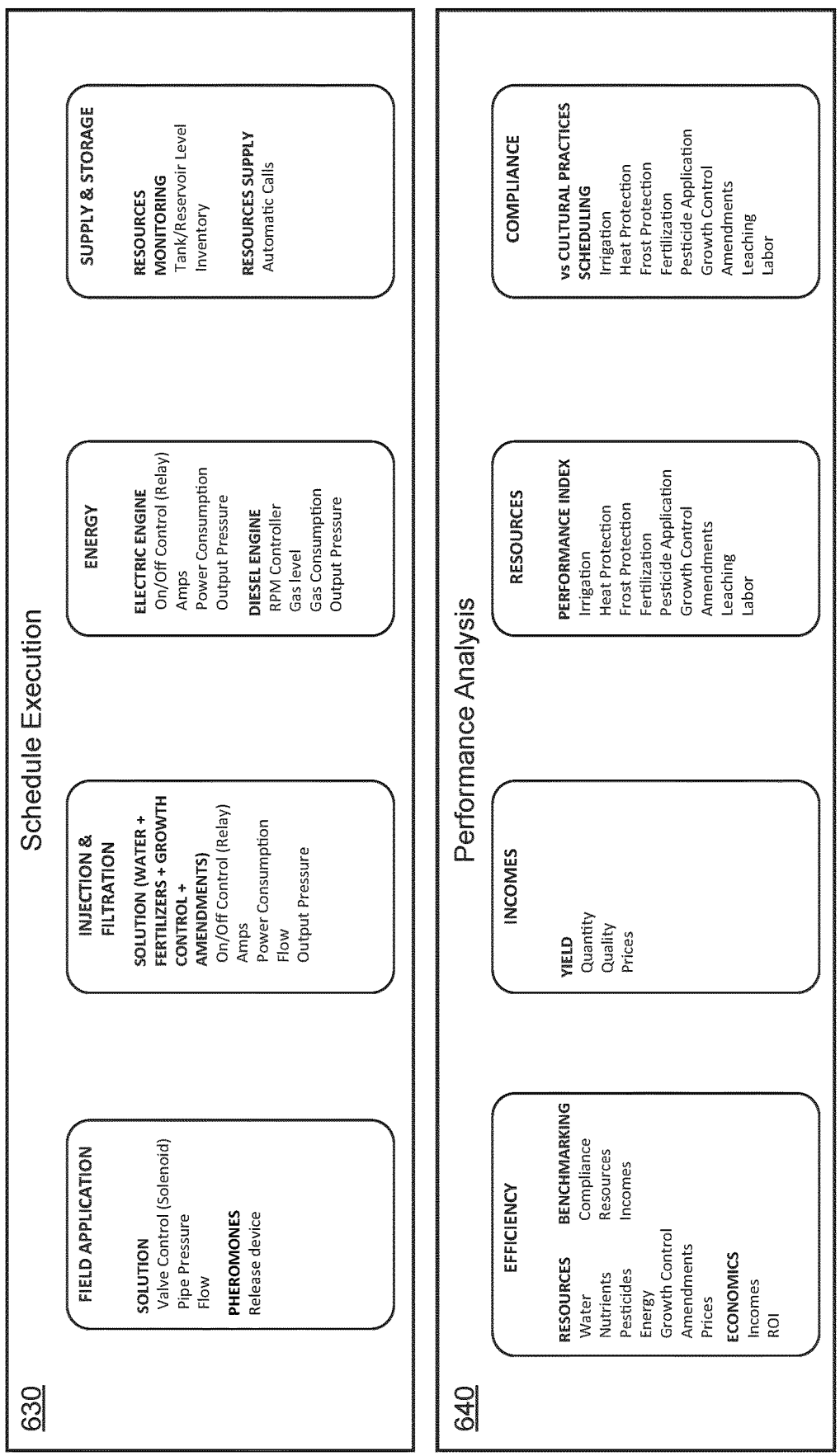

FIGS. 6A through 6C are block diagrams, shown generally as 600, illustrating four example phases of a method for monitoring and regulating plant productivity according to one or more illustrative aspects of the disclosure, and the types of data that may be received, collected, computed, controlled, output, and/or otherwise processed in the respective phases. It should be emphasized that the items identified in these Figures (particularly in FIGS. 6B and 6C) are provided and described herein as examples only, and are not intended to be exhaustive or limiting in any way.

A first phase 610 (FIGS. 6A and 6B) may be referred to as a model feeding phase. Numerous types of data, including sensor data (e.g., field monitoring data; see also FIG. 4 and the accompanying description), external data (e.g., site description data), and/or other data items (e.g., remote sensor data) may be measured or otherwise obtained for further processing (e.g., by computing system 440 of FIG. 4).

A second phase 620 (FIGS. 6A and 6B) may be referred to as an action plan or schedule computation phase. As will be discussed in further detail with reference to subsequent Figures, additional data may be calculated (e.g., feature generation) based on data received at the first phase 610. Statistical models and/or machine learning algorithms may be employed to determine an optimized action plan or schedule for controlling the environment (e.g., via controllable devices) at the site of interest. User interactions between the system and users may be facilitated, where user input may be considered in the determination of the optimized action plan or schedule.

A third phase 630 (FIGS. 6A and 6C) may be referred to as an action plan or schedule execution phase. As will be discussed in further detail with reference to subsequent Figures, various equipment, machinery, and other devices (e.g., controllable devices 452 of FIG. 4) may be controlled by the system to execute (e.g., in an automated manner, or potentially in a semi-automated manner allowing for some degree of user control) the optimized action plan or schedule determined at the second phase 620. This may entail, for example, the controlled injection of water and fertilizers, and scheduling tasks for optimal energy consumption. Automated inventory management tasks may also be performed by the system in this third phase 630.

A fourth phase 640 (FIGS. 6A and 6C) may be referred to as a performance analysis phase. As will be discussed in further detail with reference to subsequent Figures, various analyses may be conducted and reported to the user. Certain data reported in this phase may be provided that reflect the current state of plant productivity (e.g., crop yield) at the site of interest. Data may also be provided in relation to historical data and/or future projections relating to plant productivity at the site of interest. By way of further example, resource (e.g., water, nutrients, energy, labour etc.) levels and usage may also be reported.

Where changes in the environment and plant productivity may be affected, at least in part, due to the action plan or schedule executed at the third phase 630, at least some of the data (see first phase 610) used as input to the system (e.g., as processed at second phase 620) will undergo change, thus providing a natural feedback loop (e.g., as shown in FIG. 6A). The feedback may also be received directly via one or more field sensors, for example. Accordingly, at least some embodiments of a method of monitoring and regulating plant productivity will involve continuous cycling through the four phases. However, it should be noted that the number of phases, the sequence of phases, the descriptive categories identified, the processing performed at each phase, and the data processed at each phase, as may be described with reference to FIGS. 6A through 6C and other Figures are provided for illustration purposes; persons skilled in the art will understand that modifications to the number of phases, the sequence of phases, the identified categories, the processing performed at each phase, and/or the data processed at each phase may be defined differently in variant implementations. This may include, for example, the combining and/or distribution of certain processing tasks across the same or a different number of phases; the consideration of fewer, additional, and/or different data items; variations in the ordering of certain tasks or computations (e.g., certain tasks may be performed in a different sequence and/or certain tasks may be sequenced to allow for parallel computation, potentially on different processing units, etc.), and so on. By way of further example, in at least some embodiments, a given phase as depicted in any of FIGS. 6A through 6C need not be completed in its entirety for a given iteration before tasks for a different phase in a different iteration are initiated. In certain embodiments, a system for monitoring and regulating plant productivity as further described herein may be adapted to automatically determine that monitoring of a certain data no longer needs to be performed at a particular point in time, and accordingly abandon collection and/or logging of this type of data. Similarly, if certain data is not, or no longer being, collected and/or logged, the system may be adapted to determine that monitoring of the data needs to be collected (or collection needs to resume) from a particular point in time onward, and accordingly initiate (or re-initiate) the collection and/or logging of this type of data.

Figure 7:
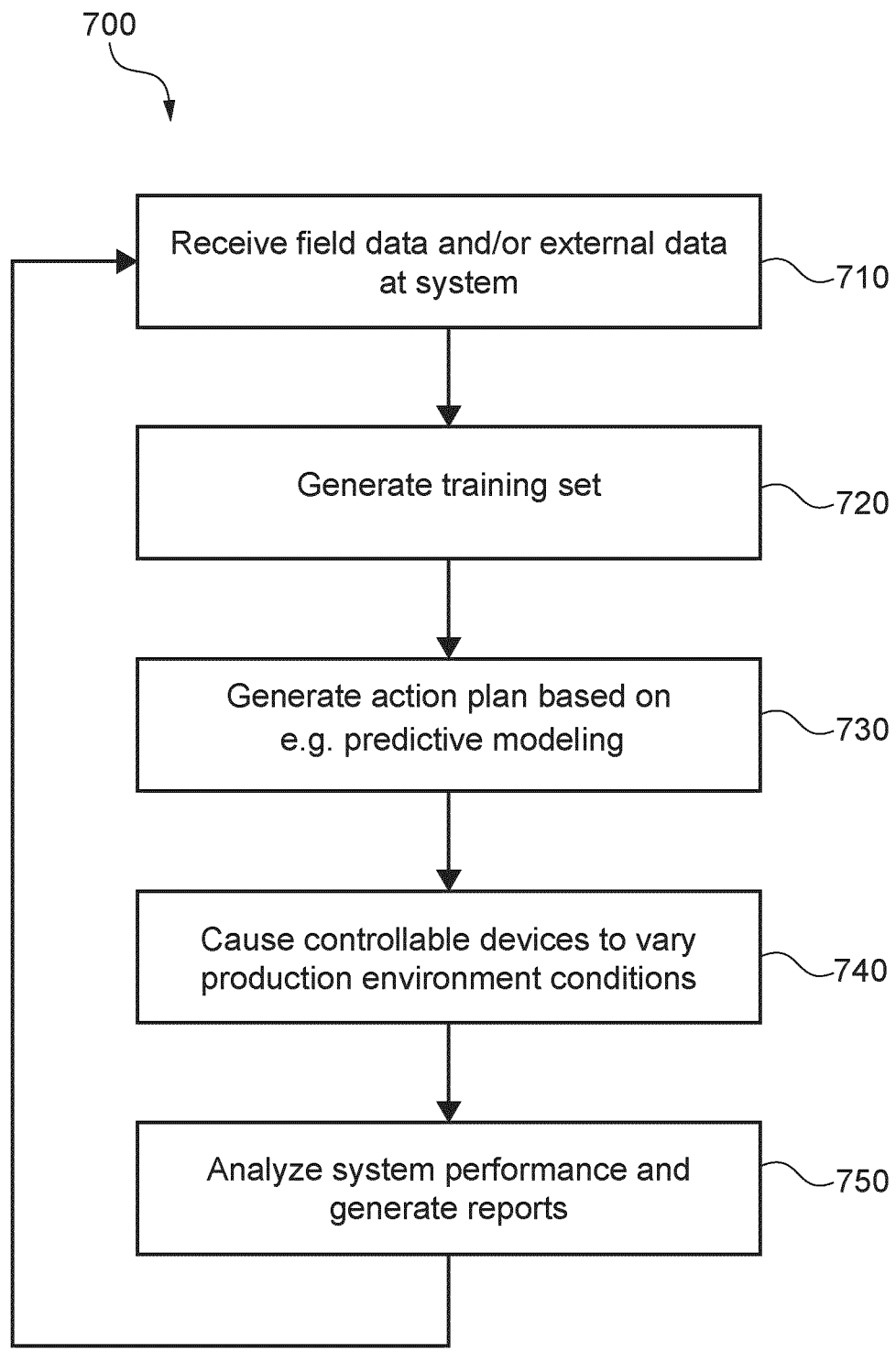
FIG. 7 is a flow diagram directed to a method of monitoring and regulating plant productivity according to one or more illustrative aspects of the disclosure.

FIG. 7 is a flow diagram of a method, shown generally as 700, for monitoring and regulating plant productivity according to one or more illustrative aspects of the disclosure. In one or more embodiments, method 700 or one or more acts thereof may be performed by one or more computing devices or entities. For example, one or more acts of method 700 may be performed by components of the computing system 440 of FIG. 4, or the computing device 100 of FIG. 1. Method 700 or one or more acts thereof may be embodied in computer-executable instructions stored on computer-readable media, such as a non-transitory computer-readable medium. Some acts or portions of acts in the flow diagram may be omitted, or performed in a different order.

At 710, field data (e.g., 430 of FIG. 4) and/or external data (e.g., 450 of FIG. 4) may be received. The field data may be measured by sensors located at a site of interest ("field"). For example, a plurality of measurements indicative of system performance (e.g., as relating to communication, power, functioning of electronics, etc.) of transmitters and sensors may be received, and may potentially be used to identify and/or predict instances and/or causes of equipment malfunction. The received data may undergo additional pre-processing, including for example, standardization and/or data cleaning. Validation of the received data may also be performed at 710. This task may correspond with first phase 610 of FIG. 6. Further details in relation to this task will be described below with reference to FIG. 8.

At 720, a training set comprising data for training (e.g., machine learning) models may be generated. The field data and/or external data (e.g., comprising historical data) received at 710 may be used to generate the training set. Additional data (e.g., features) may be derived or otherwise generated from the field data and/or external data received at 710, for inclusion in the training set. Conversely, data for certain features may be selectively excluded from the training set (e.g., through dimension reduction). Computing system 440 in its course of operation may determine that certain features are to be excluded. This task may correspond with second phase 620 of FIG. 6. Further details in relation to this task will be described below with reference to FIG. 9.

At 730, data from the training set generated at 720 may be employed to generate an action plan or schedule. This may entail determining optimal values for various controllable factors under certain constraints, as well as a set of corresponding actions to optimize plant productivity. Interactions between variables associated with plant productivity may be accounted for, and predicted values for one or more variables associated with plant productivity may be computed. For example, at least some data from the training set may be used to train a machine learning algorithm and/or to build a statistical model, which may then be used to generate predictions for variables of interest. This task may correspond with second phase 620 of FIG. 6. Further details in relation to this task will be described below with reference to FIG. 12.

By way of example, where the system is arranged to generate an action plan taking into account data relating to parameters, such as soil tension and soil salinity, methods of the present technology may comprise assessing different models for the two parameters individually, as well as assessing the interaction between all combinations of models for soil tension and soil salinity for different contexts. A context is a combination of a crop, a region, a development stage, an environmental condition, etc. The assessments ("metrics") are saved in a multi-dimensional matrix for the different contexts for soil tension and soil salinity individually, as well as soil tension and soil salinity tested in combination. The metrics used can be mean absolute error (MAE), root mean squared error (RMSE), or the like. The system computes a forecast for soil tension and soil salinity to provide an action plan in a specific context. This is generated based on a selection of the best models according to the prior assessments. An optimizer may be used to generate the action plan based on the least negative impacts. When a new context is detected or a predetermined threshold is reached, the system re-calculates the forecast for the parameters taking into account the new context or the updated threshold. At least some of these operations may be performed in parallel with one another. At least some of these operations may be pre-computed, in order to increase the performance of the system in real-time.

At 740, the action plan or schedule generated at 730 is executed. This may entail causing controllable devices (e.g., 452 of FIG. 4) to vary plant production environment conditions in accordance with the action plan. For example, an irrigation system may be instructed to operate in accordance with the action plan. This task may correspond with third phase 630 of FIG. 6. Further details in relation to this task will be described below with reference to FIG. 13.

At 750, performance of the plant productivity system may be analyzed, and associated reports may be generated. This task may correspond with fourth phase 640 of FIG. 6. Further details in relation to this task will be described below with reference to FIG. 14.

Figure 8:
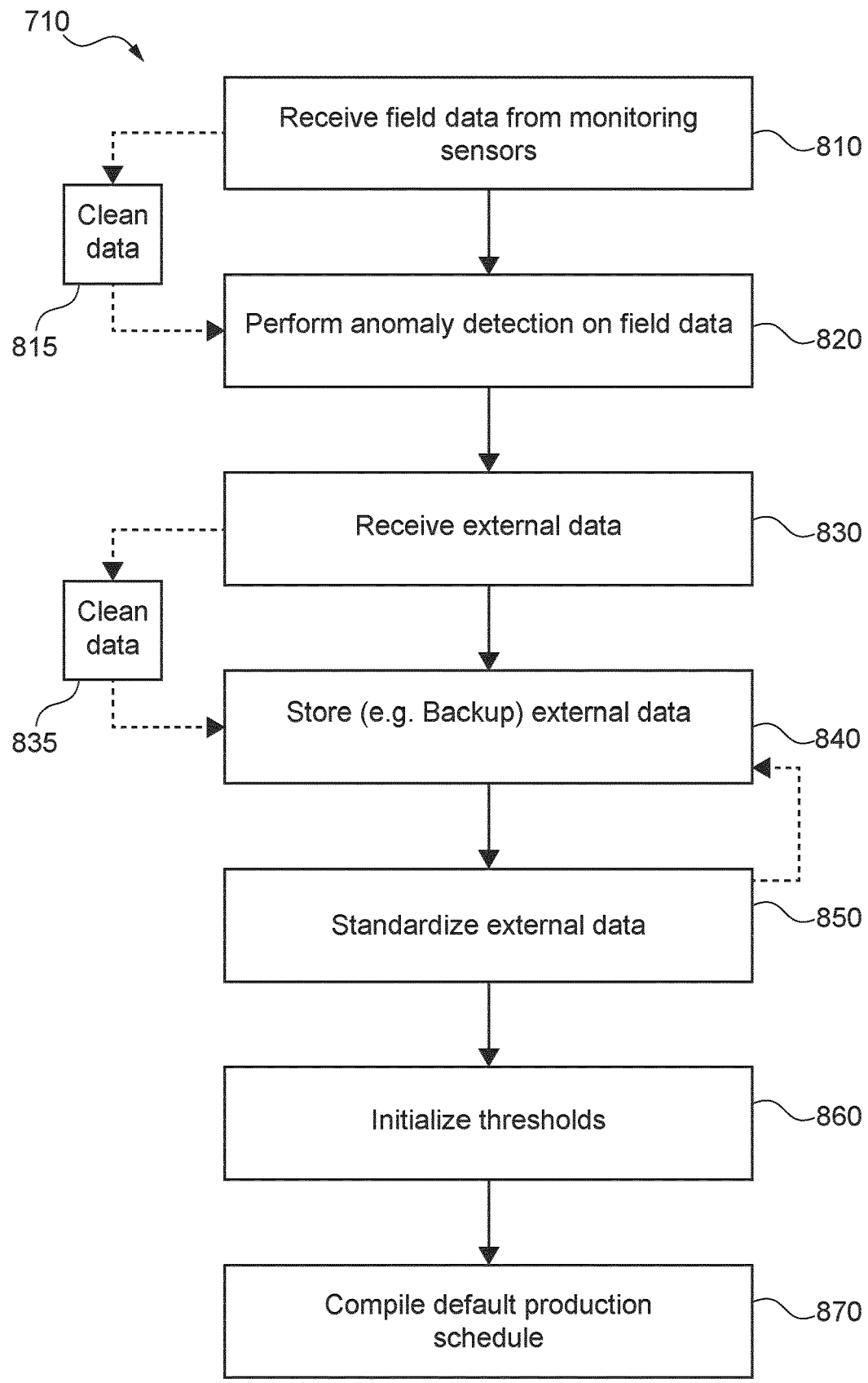
FIG. 8 is a flow diagram directed to a method of processing field data and external data according to one or more illustrative aspects of the disclosure.

FIG. 8 is a flow diagram for illustrating further aspects of 710 of method 700 in at least one example embodiment. One or more acts thereof may be performed by one or more computing devices or entities; one or more acts thereof may be embodied in computer-executable instructions stored on computer-readable media, such as a non-transitory computer-readable medium. Some acts or portions thereof may be omitted or performed in a different order.

At 810, field data is received from sensors, such as monitoring sensors 420 (FIG. 4). Data may undergo certain pre-processing acts (e.g., data cleaning), as shown at 815.

At 820, anomaly detection may be performed on data, such as the field data received at 810. One or more algorithms or machine learning techniques may be employed to perform the anomaly detection. For example, regression trees, cluster analyses, various time series analyses and/or deep learning approaches may be performed to identify anomalies in the data.

At 830, external data (e.g., comprising historical data) may be received. Sources of external data may include, for example, satellite image data, topographic survey data, soil map data, and weather forecast data (see also FIG. 4 and FIG. 6 and the accompanying description for further examples). Data may undergo certain pre-processing acts (e.g., data cleaning), as shown at 825.

At 840, external data received at 830 may be stored (e.g., for backup and/or archival purposes). For example, the received external data may be stored in a database, which may reside in whole or in part on remote devices (e.g., cloud storage).

At 850, external data received at 830 may be standardized. To standardize the data, the data may be aligned spatially and temporally, such as via intelligent interpolation and/or extrapolation, which may result in the creation of additional data. The standardization technique employed may be specific to a type of data being standardized. Expert systems may be employed to assist in determining how standardization may be performed.

At 860, thresholds may be initialized, such as productivity thresholds. Thresholds may be initialized for each of a set of variables taking into account the given crop, growth stage and geographical area, soil type, etc. Known and/or historical data may be retrieved from external data, such as scientific literature or other data, to assist in setting the initial threshold. Some thresholds may also be user-supplied. Some thresholds may also be inferred or learned by the system (e.g., as a result of a previous execution of a machine learning algorithm and/or training of a machine learning module). Some thresholds may be determined based on an analysis of similar situations at one or more other sites.

At 870, a default production schedule is compiled. The production schedule may indicate operation projections for the current or upcoming season. The production schedule may comprise information regarding cutting, sowing, tillage, maintenance of infrastructure and machine, harvesting, or other operations that may impact plant productivity.

Figure 9:
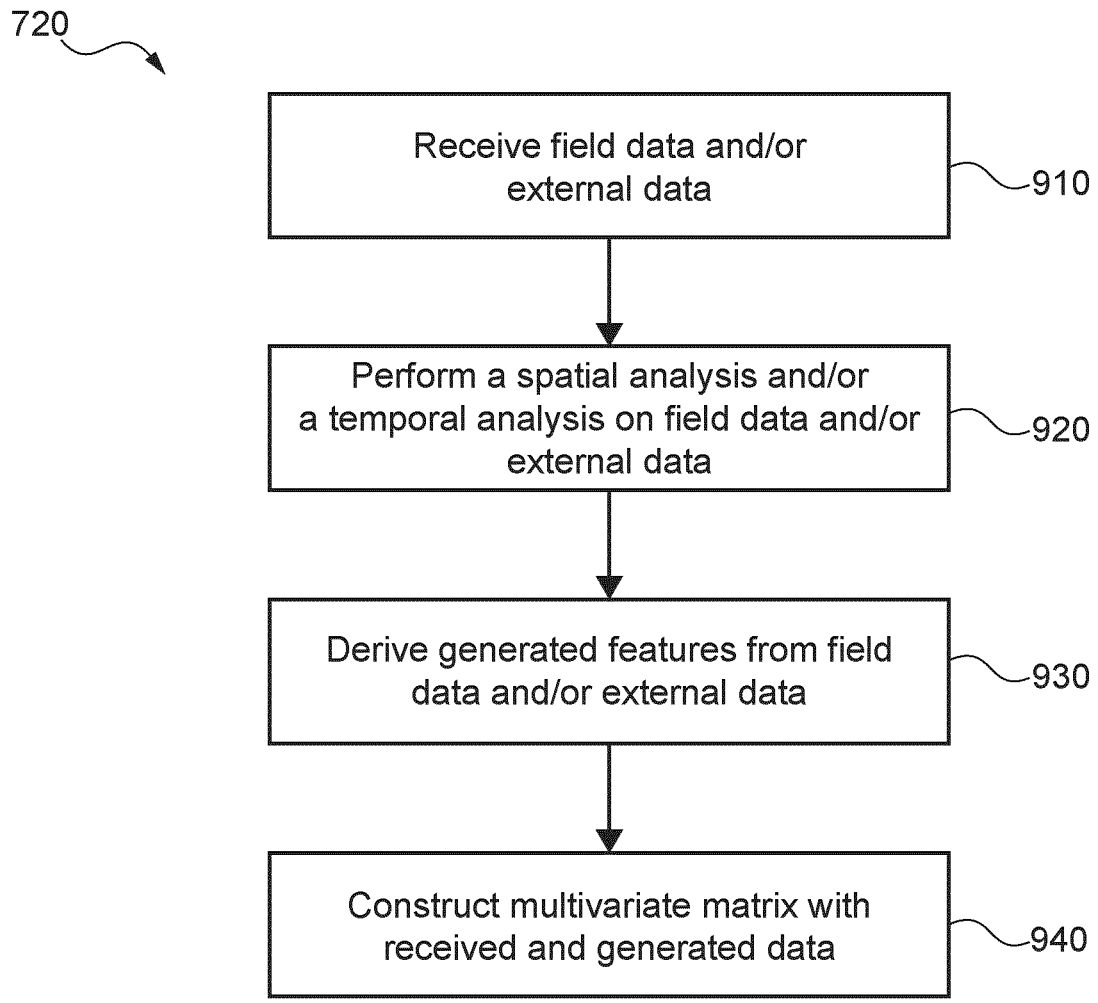
FIG. 9 is a flow diagram directed to a method of preparing training data according to one or more illustrative aspects of the disclosure.

FIG. 9 is a flow diagram for illustrating further aspects of 720 of method 700 in at least one example embodiment. One or more acts thereof may be performed by one or more computing devices or entities; one or more acts thereof may be embodied in computer-executable instructions stored on computer-readable media, such as a non-transitory computer-readable medium. Some acts or portions thereof may be omitted or performed in a different order.

At 910, field data and/or external data may be received. The received data may have been processed, for example, by performing one or more acts of 710 (see FIG. 7 and FIG. 8). Where data for primary variables may be collected directly from the site of interest (e.g., via sensors 420 of FIG. 4) or obtained from external sources, calculations may be performed to generate additional data, which may be referred to as secondary variables. This task may also be referred to as feature generation.

Secondary variables may be calculated from two or more primary or external variables. Secondary variables may also be generated not only by combining primary variables but also by further combining secondary and primary variables together, or secondary and tertiary variables together, and so on. For ease of exposition, data that is derived directly or indirectly from a primary variable is referred to herein as a secondary variable.

Each secondary variable may represent a factor that can be complementary to or different from the variables on which the secondary variable is based, and their construction may assist in optimizing the performance of learning algorithms. For example, secondary variables may comprise growing degree days, vapor pressure deficit, evapotranspiration (ET), etc.

At 920, a spatial and/or temporal analysis may be performed on some or all data received at 910. The analyses performed may comprise a clustering, classification, and/or similarity analysis. An appropriate model may be selected from a database for application to a first iteration of data, thereby initiating a learning process. The analysis may be performed for each newly implanted site.

At 930, generated features may be derived from the field data and/or external data received at 910. Automated feature identification of spatio-temporal series of all variables may be performed. Temporal and spatial analyses may be performed to synthesize information in the form of multiple parameters. These multiple parameters may be saved in a multidimensional matrix. As used herein, the parameters refer to elements, activities or conditions of the productivity system or its environment that influence plant productivity and that can be measured or defined by one or more variables. Examples of parameters include, but are not limited to, crop requirements for water, requirements for nutrients, and the occurrence or presence of disease and pests ("m & r"). Such parameters are each assessed by several measured or calculated variables.

Figure 10:
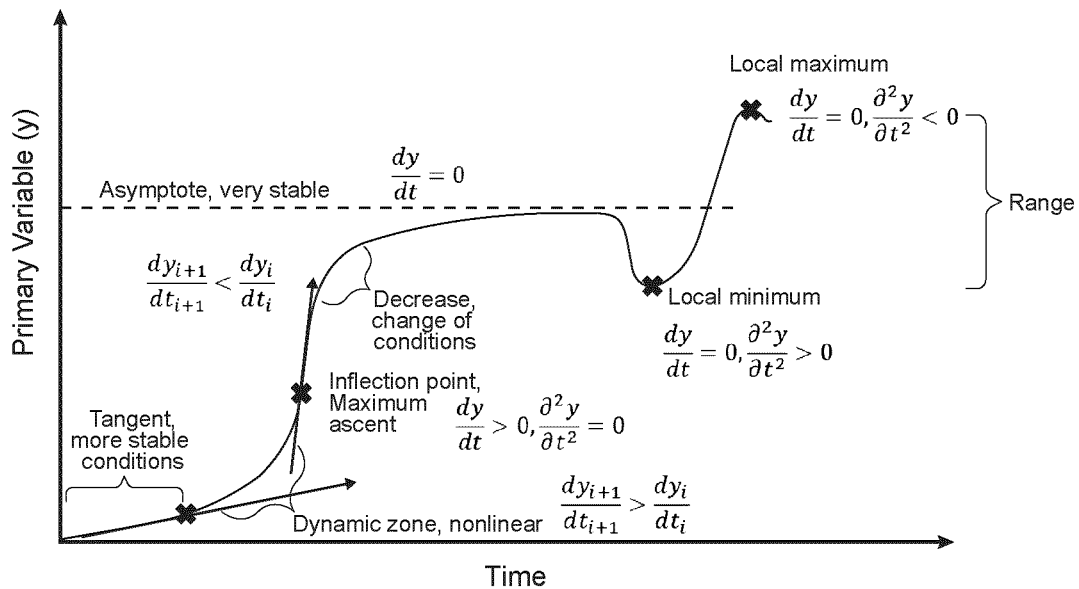
FIG. 10 is a diagram illustrating analysis of a time series according to one or more illustrative aspects of the disclosure.
Figure 11:
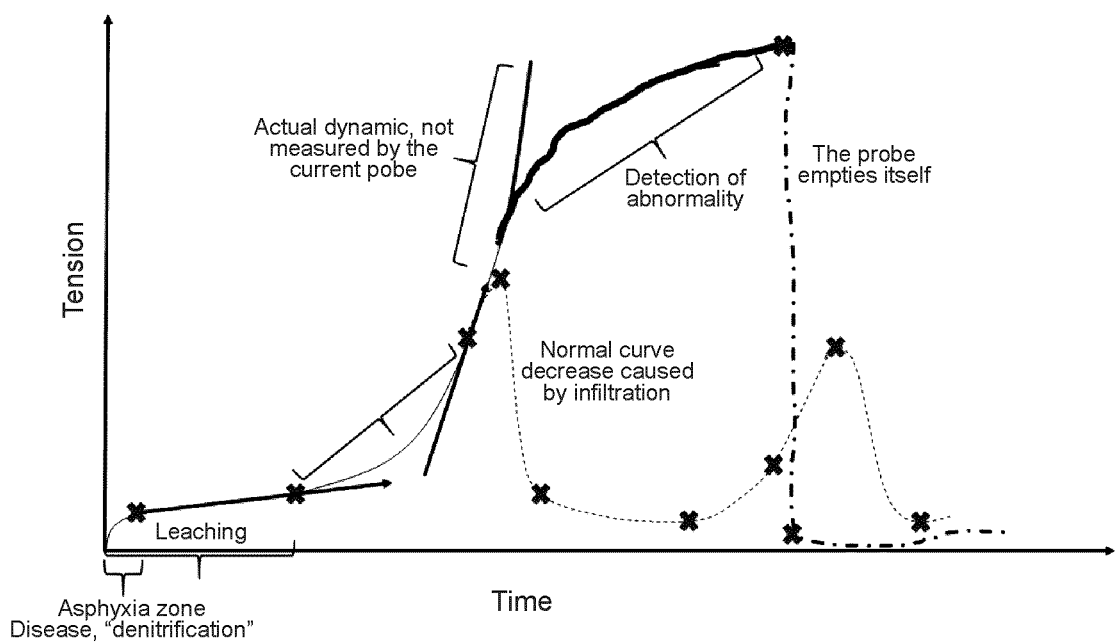
FIG. 11 is an example graph in which tension data is plotted against time.

The system may also allow for the identification of circumstances that are causing variables to reach critical limits Various characteristics of a given time series may be assessed to identify these circumstances and how they cause the variables to reach their critical limits, including but not limited to: local minima and maxima, inflection points, amplitude, variance, mean, first-, second-, and higher-order derivatives, trend, frequency, autocorrelation structure, seasonality, stationarity, Fourier transformation, wavelet decomposition, fractal analyzes, past values, etc. (see e.g., FIG. 10 in which an example method of dissecting a time series for a given variable is shown). The variables at a given time series may be dissected in order to distinguish different nonlinear dynamic phases or patterns associated with the identified circumstances. In some instances, the circumstances come about or are set forth because of interplay between several variables. For example, FIG. 11 illustrates how a decomposition of a time series with respect to tension can assist in identifying the dynamics of certain phenomenon that affect that variable. In the case of tension, the history of soil drainage and wetting cycles, weather conditions, type of crop, physiological stage, presence of disease or insects, soil temperature, salinity, etc., may have an impact. As for any other variables, tension is influenced by the interplay amongst all other variables, whether they are current, past or future.

At 940, one or more multivariate matrices are constructed to store the data (e.g., whether obtained directly from sensors or an external source, or through a process of feature generation) on which learning models will be subsequently trained.

Figure 12:
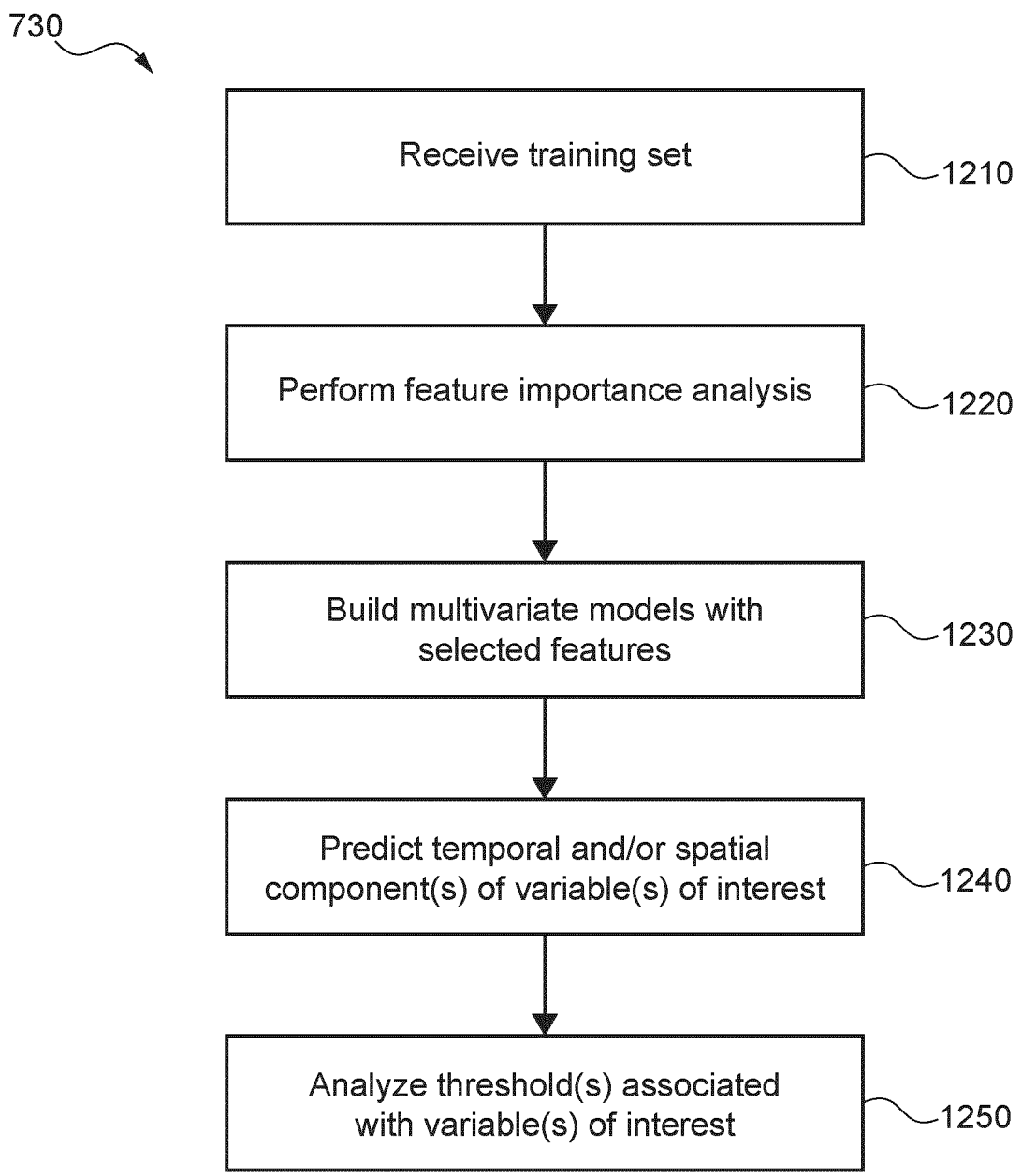
FIG. 12 is a flow diagram directed to a method of generating an action plan based on one or more models according to one or more illustrative aspects of the disclosure.

FIG. 12 is a flow diagram for illustrating further aspects of 730 of method 700 in at least one example embodiment. One or more acts thereof may be performed by one or more computing devices or entities; one or more acts thereof may be embodied in computer-executable instructions stored on computer-readable media, such as a non-transitory computer-readable medium. Some acts or portions thereof may be omitted or performed in a different order.

At 1210, a training set comprising training data may be received. This may be in the form of one or multivariate matrices, as may have been generated at 940 (FIG. 9). At 1220, feature importance analyses may be performed. Features, or characteristics, may be identified and selected. A relational and multi-model structure may be defined. Features may be ranked or grouped based on an importance to plant productivity. The ranking of features may be performed using local and global sensitivity, regression trees, classification, grouping, correlation matrices, principal components, multidimensional positioning, and/or sequential regression, among other techniques. Feature ranking may aid in model interpretation, and may also be employed in order to identify a smaller subset of data that may be subsequently used to increase efficiency when model training, for example. Different results may be independently integrated to select features. These selected features may be used to define the relational structure of multivariate models. Relationships between the features may be identified during the feature importance analysis. A logical structure for use in the definition of multivariate models may be determined. These multivariate models may be used to predict variables.

At 1230, one or more multivariate models may be generated. This may involve application of various machine learning algorithms and/or the building of statistical models. Various statistical techniques (analysis of variance, linear and nonlinear regression, semivariogram), compositional analyzes, solutions of differential and integral equations, volume and finite elements, use of neural networks (e.g., deep learning), support vector machines, and/or other algorithms may be employed.

At 1240, temporal and/or spatial components of variables of interest may be predicted, and compared to corresponding thresholds at 1250. Selection of one or more variables of interest may be performed according to a determined or expected measure of importance that may be relevant for a particular action and/or activity. For example, in nutrient management, 'Nitrates' may be considered as the most important variable. Thresholds for self-regulation of a productivity zone may be determined and prioritized. Hierarchization may be performed using iterative optimization methods based on simulations combined with sensitivity analyses, decision trees, risk analyses, and/or other methods for prioritizing actions. The thresholds may be designed to optimize positive effects on all variables simultaneously, which may minimize negative effects on the variables.

Priorities for action may be determined even when more than one variable would benefit from intervention. Schedules of intervention may be produced that meet multiple thresholds simultaneously. The schedules of intervention may also satisfy other constraints, such as infrastructure constraints, personal constraints, or economic constraints. These constraints may be varied and may be caused by a production infrastructure that does not support the automation of certain components, such as staff schedules, accessibility to limited inputs (such as water, fertilization, pesticide, and/or energy), and/or operating costs and projections on sale prices, among other constraints.

A logical sequence of operations of the prioritized actions may be generated. The sequence of operations may be in the form of a production schedule, or the sequence of operations may be used to generate the production schedule. The production schedule may be continuously updated, or updated at a set interval.

By way of example, two examples of constraints may be: (1) cannot irrigate on the weekend as there is no irrigator available; (2) pump X has the capacity to irrigate only 100 acres at the time. In this context, a user may be given the choice (in contrast to situations where consideration the system is configured to learn how to consider these constraints) to optimizing the schedule according to each constraint. For example, the user may be able to provide input that reflects a response to the prompt: "If an irrigation event is scheduled for Sunday, do you want to postpone it to Monday or perform it earlier on Friday?"

Two other examples of constraints may be: (1) a level of nitrates in the soil exceeding the level permitted by law and/or regulations which would prevent fertigation as a mediating means or (2) in water stress conditions, restrictions on the use of water that would prevent irrigation from being performed. After being fed with one of these constraints, the system would consider and suggest to the user an alternative intervention to mitigate the level of stress and maintain the plant productivity based on the analysis of other field data and/or interactions between multiple factors of the field data and/or generated data.

Figure 13:
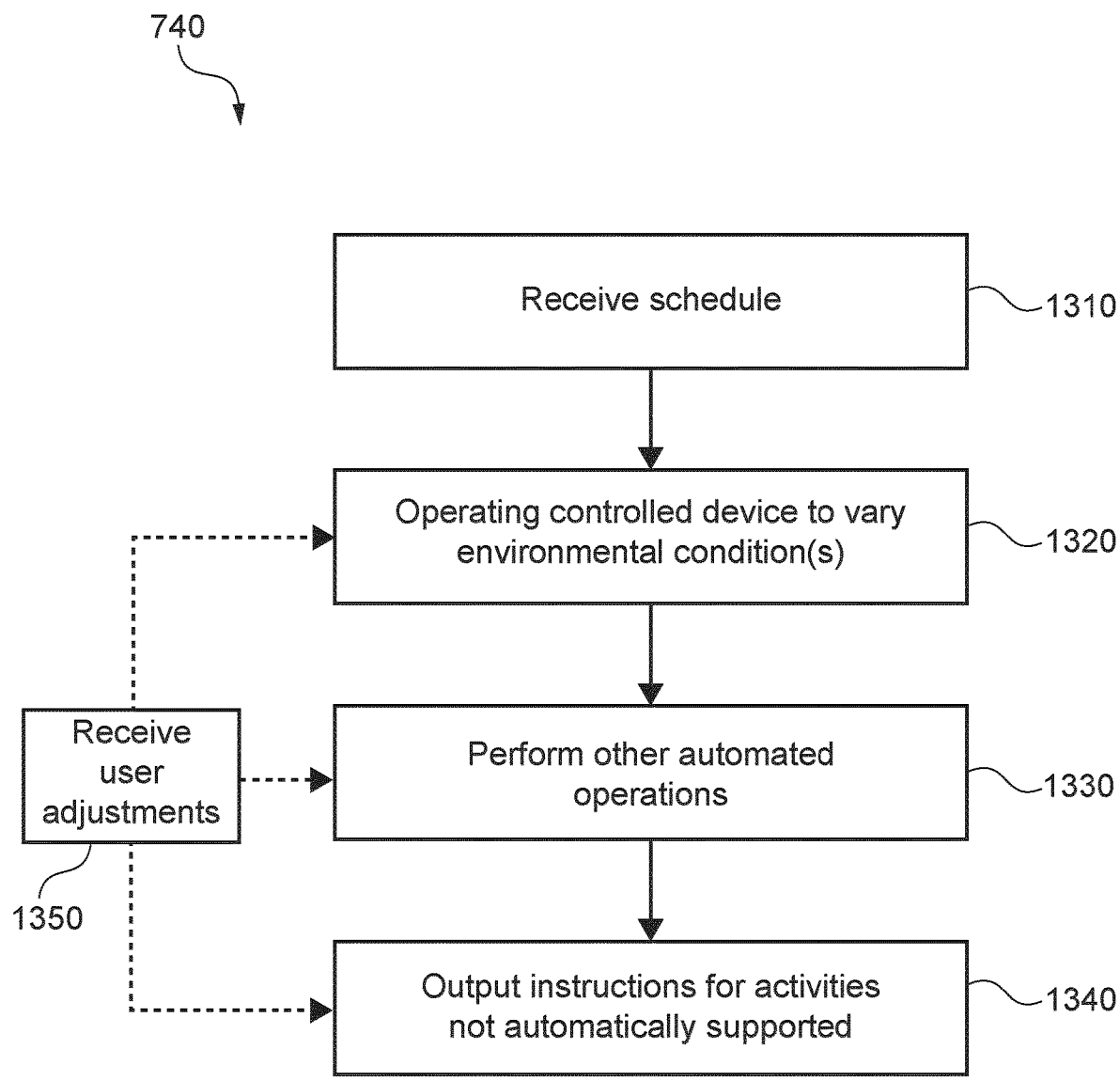
FIG. 13 is a flow diagram directed to a method of controlling devices to vary environment conditions according to one or more illustrative aspects of the disclosure.

FIG. 13 is a flow diagram illustrating further aspects of 740 of method 700 in at least one example embodiment. One or more acts thereof may be performed by one or more computing devices or entities; one or more acts thereof may be embodied in computer-executable instructions stored on computer-readable media, such as a non-transitory computer-readable medium. Some acts or portions thereof may be omitted or performed in a different order.

At 1310, a schedule (or action plan) may be received. The received schedule may be a schedule generated from the output of 730 (see FIG. 7 and FIG. 12). The schedule may indicate various activities to be performed. The schedule may comprise activities that can be performed automatically and/or activities that can be performed by users. The operating schedules may be directed to automated operations, input orders, agronomic recommendations, and instructions for activities not automatically supported.

At 1320, controllable devices (e.g., 452 of FIG. 4) may be operated to automatically vary environmental conditions. The schedule received at 1310 may comprise information for operating these controlled devices.

At 1330, other automated operations may be performed. For example, an automated process to fill a reservoir/tank with water, fuel, fertilizers, etc., to order fertilizers, and/or to keep a pump primed to be ready to start when needed, may be initialized.

At 1340, user instructions may be output for activities that are not automatically supported. The instructions may relate to, for example, input management or maintenance of production infrastructure, such as inventory of inputs for preparing orders, filling of water tanks, and status and quality of water for irrigation. The instructions may comprise a schedule for activities to be performed by users. The instructions may comprise recommendations, intervention requests, risk indices, warnings, or any other type of instruction or notification.

User adjustments may be made to the schedule at 1350. Prior to any automated or non-automated action being applied or recommended (see e.g., 1320 through 1340), the user may be prompted and/or permitted to make operational adjustments. For example, the schedule may be output to the user by a user interface, and adjustments to the schedule may be received by the user interface.

Figure 14:
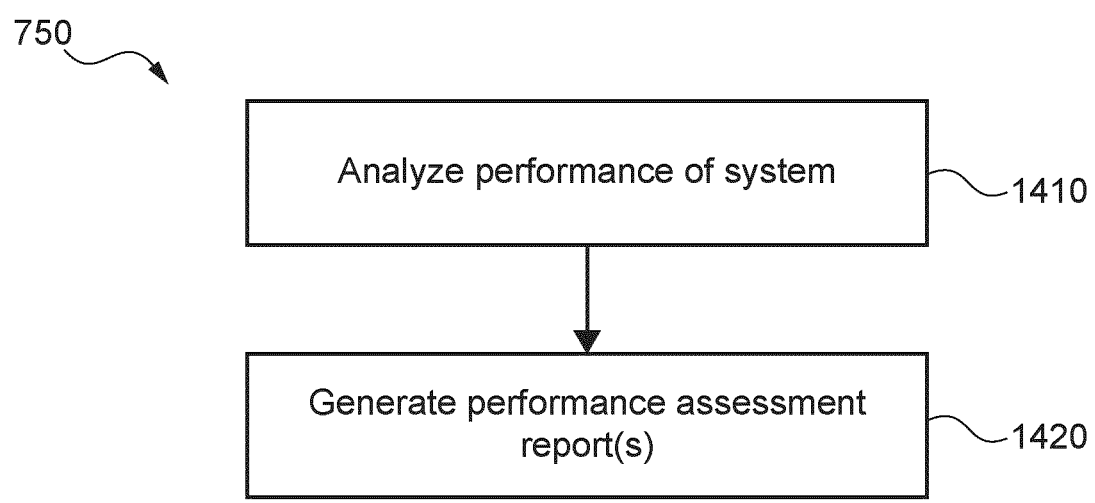
FIG. 14 is a flow diagram directed to a method of reporting according to one or more illustrative aspects of the disclosure.

FIG. 14 is a flow diagram for illustrating further aspects of 750 of method 700 in at least one example embodiment. One or more acts thereof may be performed by one or more computing devices or entities; one or more acts thereof may be embodied in computer-executable instructions stored on computer-readable media, such as a non-transitory computer-readable medium. Some acts or portions thereof may be omitted or performed in a different order.

At 1410, performance of the plant productivity system may be analyzed. A complete assessment of system performance and efficiency may be performed. The performance analysis may comprise compiling all available variables, such as real-time measurements, descriptive variables, external data, and secondary variables in relation to the determined thresholds and schedule, to generate and output performance data and/or reports to a system user at 1410, potentially for display in a dashboard via a user interface, in printed form, or some other output format. For example, the system may learn that limitations on pumping capacity may be having a greater cost impact than the cost of purchasing a bigger pump that would increase pumping capacity.

Measures or indicators of yields or potential yields may be available during the growing season and/or at the end of harvest, and these measures or indicators may be used to improve the models used by the system. For example, thresholds may be adjusted depending on new data received; operations may also be modified based on user input in response to displayed information.

The assessment may determine that additional data would improve the performance of the system. The assessment may comprise determining whether sensors or other equipment should be added or removed from the system. For example, if in the process of determining the importance of each of multiple variables, if a variable measured by a sensor is determined to have no or negligible impact on the model, the system may recommend removal of this sensor. As a further example, it may be determined that two devices are reporting the exact same data in two side-by-side fields; the system may recommend removal of one of the two devices.

Levels of compliance may be calculated for relevant parameters with regards to the objectives and schedule. The resources used may be assessed, such as the amounts of energy and inputs. Technical and economic performance may be defined through the provision of statistics of efficiency, and of available indices of comparable regional crops, past performances, or any other comparable for reference. A retroactive loop of system performance may be implemented to continuously optimize algorithms used in the plant productivity system based on newly acquired data. Models may be retrained at pre-set intervals (e.g. daily), taking into account new training data. Through these assessments, precise thresholds of self-regulation may be determined.

Example

To more clearly illustrate how certain embodiments described herein may be put into effect, a fictitious example implementation of a plant productivity control system according to one or more illustrative aspects of the disclosure will now be described with reference to FIGS. 15A through 15C. These details are provided for illustrative purposes only, and should not be construed as limiting embodiments in any way. In particular, variant implementations need not contain all of the features, or any particular combination of features, described in this example.

Provided herein are details of a case study based on a 4 year old 40-acre block of almonds located in the Central Valley of California. The crop is managed by traditional crop management method. The soil surface is relatively flat and the soil comprises homogeneous loamy sand in the first 3 feet, which corresponds to the depth of the root zone.

The entire field is irrigated from splitting the potential weekly evapotranspiration data calculated by a public weather provider in three irrigation events. Water is pumped directly from a well equipped with an electric engine started and stopped manually (cost of $A/acre/hr). The well is 600 feet deep and water depth is 300 feet. A gypsum tank is connected to the irrigation system in order to apply gypsum to improve the water infiltration rate when it becomes limited. Because monthly water analysis from the past shows a tendency for the water coming from the well to be too basic (high pH), an acid burner has been installed. Gypsum (for improving the infiltration rate; cost of $V/hr/acre) and acid (for increasing pH and nutrient availability; cost of $B/hr/acre) are systematically injected at each irrigation event.

Fertilizers are stocked close to the pump in a 10,000-liter cylindrical tank of 3 meters height and in addition to the main irrigation pump, an injection pump needs to be turned on to provide fertigation (i.e., liquid fertilizer delivered via the irrigation system) at a cost of $Z/acre/h. A fertigation program built by an agronomist ($T/acre/yr) from soil and leave samples analyzed at the beginning of the season is given to the grower and consists basically of one fertigation event per week.

Hives are installed along the perimeter of the field during the flowering period to help with pollination. Pesticides can be applied ($C/acre) in the field with a motorized vehicle driven by a worker when the Pest Control Advisor (PCA) recommends spraying following his weekly scouting ($U/acre/yr). Even if 3 full time workers are necessary to accomplish all the tasks above, a crew of only 2 workers is available from 7:00 AM to 4:00 PM from Monday to Friday (cost of $D/hr/worker) due to labor scarcity in the area. During periods of overtime work, the cost increase to 1.5*$D/hr/worker. While scouting, the PCA also takes note on weeds coverage. The income from the yields is estimated at the beginning of the season to be $E/lb at harvest. Table 1 below outlines the particulars of the case study:

TABLE 1

Particulars of case study

| Operation | Cost (w/Traditional Management) | Cost (w/the System) |
| --- | --- | --- |
| Irrigation | $A/acre/hr | $A/acre/hr - 0.25 * $D/acre/hr |
| Gypsum Injection | $V/acre/hr | $V/acre/hr |
| Acid Burner | $B/acre/hr | $B/acre/hr |
| Fertigation | $Z/acre/hr | $Z/acre/hr - 0.25 * $D/acre/hr |
| Pesticide application | $C/acre/event | $C/acre/event |
| Advising and labor | Cost | |
| Scouting | $U/acre/yr | 0 |
| Fertigation Program | $T/acre/yr | 0 |

TABLE 1-continued

Particulars of case study

| | | |
|---|---|---|
| Labor (regular hours) | $D/hr/worker | $D/hr/worker |
| Labor (overtime) | 1.5 * $D/hr/worker | 1.5 * $D/hr/worker |

Income

| | |
|---|---|
| Yield | $E/lb |

The information mentioned above is provided to the plant productivity system (e.g. system 400 of FIG. 4) for determining how many stations and sensors are recommended to be installed. The pump station is equipped with relays to activate the pump, the acid burner, and the gypsum injector without human intervention. The depth of water in the well and the temperature, salinity, nitrates content, and pH of the water are monitored with appropriate sensors. A sensor for monitoring fertilizer level is also installed in the tank.

By consulting topography maps and historical satellite imagery from external sources (e.g. external data 450 of FIG. 4), the system recommends that one field station be installed in the center of the field. The station is equipped with tensiometers, soil water content probes, osmotic potential probes, nitrates sensors, and soil temperature sensors at a depth of 12 inches, 24 inches and 36 inches in the soil for monitoring the whole root zone conditions. At this station, air temperature and relative humidity are measured in the canopy. A spore and insect analyzer are installed between trees to detect and quantify spores and insects without any human intervention. A foraging bee activity counter is installed at the hives. Finally, a weather station is installed at the border of the field to measure air temperature, relative humidity, wind speed and direction, atmospheric pressure, leaf wetness, solar radiation, and rainfall.

From these variables, the system calculates secondary variables. The water fluxes in the soil are computed from the soil water content and tension data. Soil total potential is calculated from the sum of tension, osmotic, and gravitational potential data. From air temperature and relative humidity in the canopy, the vapor pressure deficit and dew point is calculated. From the weather station data, evapotranspiration, dew point, chilling hours and portions are calculated, and pest and disease development risks are evaluated (e.g., Alternaria Leaf Spot, Navel Orangeworm, Scab, Shot Hole, Coryneum Blight, etc.). The volume of fertilizer in the tank is calculated. As all the primary variables are reported continuously in real-time, the complementary variables can also be calculated continuously.

By forecasting the interplay between these multivariate dynamic variables, the system dynamically auto-adjusts the profitability thresholds (conditions) considering the income of an action against the cost of an inaction in order to predict, schedule, and operate actions (irrigation, leaching, fertigation, fertilizers supplying, water pH adjustment, etc.) to maximize crop profitability.

The system continuously confirms the impact of the schedule (action plan) by using some validation variables. Stem water potential is installed around leaves of a tree and a dendrometer is installed to measure trunk growth or shrinkage. These sensors might not be used to schedule actions as they are reactive and not predictive but the system may rely on them to validate results and strategy. External indexes such as Normalized Difference Vegetation Index (NDVI) values coming from satellite imagery may also be used to validate the effectiveness of the strategy and for extrapolating the data on a spatio-temporal basis. These images may also serve to evaluate weed coverage on the ground in order to schedule weed removal operations.

Once the equipment described above is installed, the system begins collecting data from the field. The system uses preset thresholds based on the academic literature and data obtained from other similar sites found in its database. As soon as the system collects new local data, profitability thresholds are adjusted from the learning of the system with local conditions and data. The trees are still dormant and the system considers the potential yield to still be 100% and thus, the higher potential profitability.

Figure 15A:
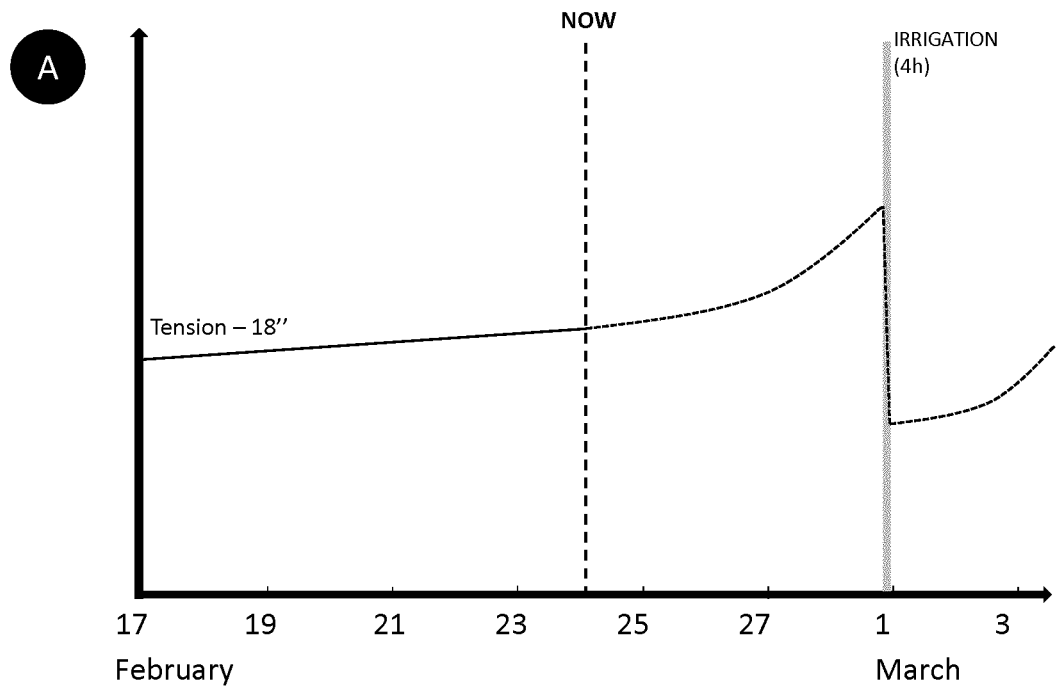
FIGS. 15A through 15C illustrate details of an example implementation of a plant productivity control system, operated according to one or more illustrative aspects of the disclosure.

FIG. 15A illustrates tension levels after one month of activity. During that month, profitability thresholds have continuously been adjusted to reflect local conditions learned by the system. The potential yield at harvest has dropped to 97% because a mechanical failure of the irrigation pump impaired irrigation during 3 days and water stress conditions were present during these days. The system learned from analyzing data in other similar sites that yield loss is reaching 1% per day when water stress occurs during trees' awakening. The water stress has been validated with dendrometer measurements as the trunk shrank during those 3 days. The system has turned the acid burner on occasionally to lower the pH when it was profitable, but has not injected gypsum yet, as the infiltration rate data analysis did not show any limitation.

The time period illustrated in FIG. 15A is in the middle of the flowering period. The farming operation schedule for the next week is the following: Nothing is planned before the 28th. On the 28th the irrigation will be run at 7:00 PM on until 11:00 PM. The last week historical data, the current data, and the forecast data that led to this schedule are shown in FIG. 15A.

Figure 15B:
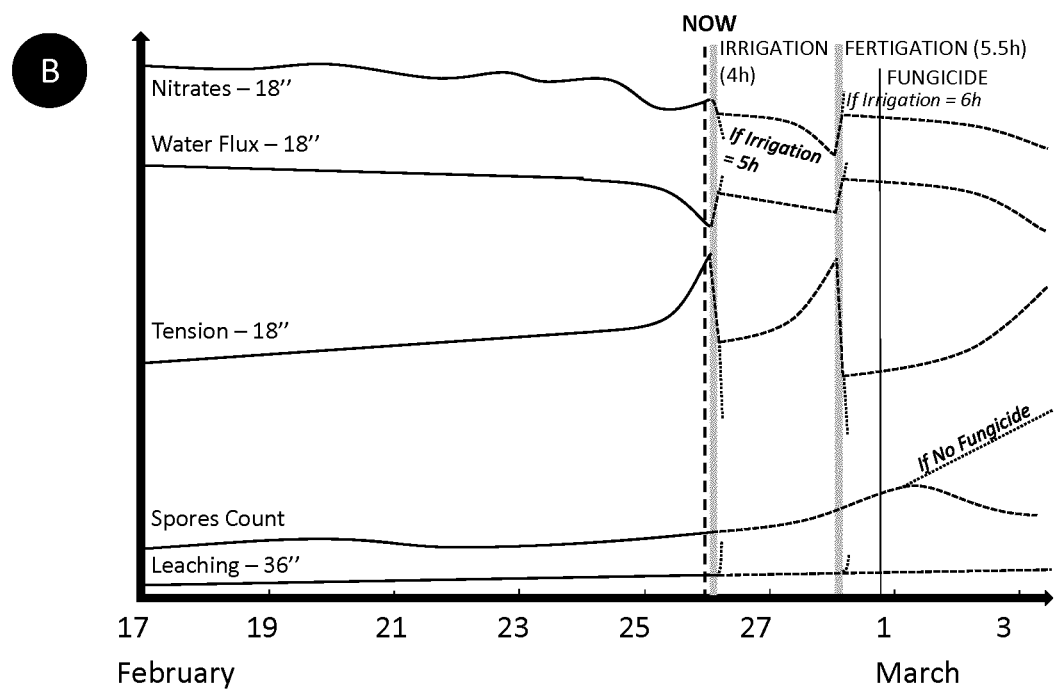

FIG. 15B illustrates the time period of February 25th at 4:00 PM. The system has been continuously verifying and validating the schedule, and the schedule illustrated in FIG. 15B has changed to run irrigation via the automated mode to apply water from 6:00 PM to 10:00 PM on the 25th, run fertigation via the automated mode at 9:30 PM on the 27th until 3:00 AM on the 28th, apply fungicide by the worker with sprayers mounted on a motorized vehicle on the 28th at 8:00 AM. No other action is scheduled for the next 7 days.

The system has considered the schedule illustrated in FIG. 15B to be optimal based on the following analysis:
  i) The pre-determined conditions for starting irrigation during the flowering period have not been reached and irrigation was not planned before the 28th, but the system is detecting a sudden change in tension and water fluxes measured in the root zone. Because the system has never faced the current conditions on this site before, this sudden change was not anticipated. However, the system recognises this sudden change (e.g., see FIG. 15B, in the context of processes depicted in FIGS. 10 and 11) to be an omen of hydric conditions to be limiting roots water uptake sufficiently to affect the yields at the end of the season by 0.1%/acre per hour of water stress conditions occurring during flowering. The system starts immediately to evaluate the profitability of triggering an irrigation event now by forecasting dynamically and simultaneously the interaction between all the multivariate variables.
  iii) Because the impact on foraging bees when micro-sprinklers are turned on for more than 15 minutes is such that the yield decreases by 0.15%/acre per hour, running irrigation would not be profitable until bees stop their activities at 6:00 PM. Without an automated system for controlling irrigation, the irrigation would have started at 7:00 AM the following day, as no workers were available before then to initiate the irrigation. That irrigation during the day would have impacted bees' activity from 8:00 AM to 12:00 PM and resulted in supplemental yield losses. In a mono-variate crop management system based only on soil tension, the optimum run time would have been computed to be 6 hours, to lower soil tension to a fixed threshold without considering the impact on pollination. With traditional crop management, all of that would have been missed. In contrast, system 400 determined the optimum run time to be 4 hours. In this particular case, the irrigation event would not have a significant impact on other variables, except the nutrients content. The pH of the water being at an optimal level, no adjustment is needed here. By considering the pumping cost of the irrigation water, the nutrients content in the soil and the cost of fertilizers injection, the system determined that 4 hours of irrigation is the longer limit in order not to push down the nitrates too fast and too deep. The system has evaluated the rate of nitrates moving down being accelerated when irrigation is longer than 4 hours. Because the nitrate content prior to irrigation was slightly low, irrigating more than 4 hours will result in the need for nutrient injection in the irrigation system. The cost of adding fertilizers is not actually profitable in these conditions compared to stopping irrigation after 4 hours.

iii) After running iterations on the scheduling process, the system scheduled a fertigation event on the 27th at 9:30 PM even though the system predicted there will be enough nutrients and water until the night of the 28th. However, a fungicide application is scheduled on the morning of the 28th at 8:00 AM and leaves will need to remain dry for the next 24 hours after the fungicide application, which means no fertigation is allowed during that interval. A worker has then been notified by the system of this new task on his schedule. The system identified the need for that fungicide application because, even if the number of spores counted by the spores sensor has been close to 0 during the last 8 days, the system is predicting the threshold where spraying is profitable to be reached in 3 days because of high winds blowing from the West where the number of spores in this area is actually very high according to the system analysis of other sites. The threshold where spraying is profitable is adjusted to a lower value compared to what it was the day before, because the external weather forecast has been refreshed and the weather conditions in 3 days are now suitable for disease development. To conclude spraying to be profitable in 3 days, the system analyzed the cost of the spraying event (labor cost+ pesticide cost+collateral cost) and determined this cost to be lower than the yield loss associated with the development of the disease on the leaves of the plant (10%/acre). In this case, the only collateral cost was the impact on pollination. The system automatically notifies the beekeeper to close the door of the hives to prevent bees foraging on treated leaves for 24 hours after spraying, which would result in a yield loss of 2.5%/acre. Spraying this pesticide prevents workers from entering in the field as the re-entry interval is 24 hours, but this is not impacting any operations because nothing was scheduled for the workers that day.

iv) Before concluding that the fertigation event will be scheduled on the night of the 27th, the system evaluated other scenarios such as postponing fertigation to Saturday (1st), but this will cause more damage (3%/acre) than scheduling it on the night of the 27th. The night of the 27th was then identified to be the most profitable scenario. The system has also simultaneously considered the impact of that fertigation event on all the other variables prior to scheduling this action. Adding nutrients will increase osmotic potential in the root zone, but total potential will still remain at an optimal level because tension will decrease. However, fertigation run time has been optimized to allow sufficient air content and avoid hypoxic stress and excessive application of nutrients. For that optimization, the system analyzed water and nitrates movement rates during and following all historical fertigation events. With exceptionally high soil, water and air temperatures predicted, the system is anticipating hydraulic conductivity to be higher than it was during irrigation on the 25th. These conditions led to a calculated runtime of 5.5 hours. If calculated with a monovariate model based only on soil tension, the run time would still have been 6 hours like it was for irrigation on the 25th, because tension is similar today to conditions on the 25th. However, a 6 hour irrigation event would have led to a loss of water and nutrients below the root zone during 0.5 hours, because water and nitrates are infiltrating faster due to the higher temperature conditions. The system did not determine that there would be any significant impact on all the other variables. The time of 9:30 PM has been computed to be the optimal time for starting the pump as the system analyzed from the leaf wetness data that the leaves need at least 5 hours to dry following an irrigation event. Because the pesticide is scheduled to be applied on dry leaves at 8:00 AM, the irrigation should be stopped prior to 3:00 AM and started no later than 9:30 PM.

v) At 7:00 PM on the 25th, the system determined that the water pumped in the 2 first hours of the irrigation event had an acceptable pH level, but the last data points showed that the pH level was quickly rising. Thus the pH needs to be lowered by the acid burner. If the pump is watering while the pH is rising, the system predicts that the soil pH will reach a threshold where nutrients uptake will be limited, causing yield loss of 0.2%/day until the next irrigation event. The system automatically starts the acid burner as the cost ($Y/acre/hr) of running it is actually lower than the yield loss associated with pumping water above the pH threshold. As the system simulated all other parameters as not being affected by the injection of acid, the rest of the schedule remains the same.

vi) At 5:00 PM on February 28th the system applied a correction to the threshold definition related to the temperature in the canopy to prevent heat stress. There was no data available in the literature about this threshold during flowering. The system analyzed data from all the sites and found large variations in the response of almond trees to heat stress during flowering even if the threshold considered the interaction of air and canopy temperatures with soil hydric and nutrient conditions. The temperature, relative humidity, and vapour pressure deficit (VPD) reached the forecast numbers in the afternoon and according to the information obtained by the system, no cooling irrigation was needed. However, the system has just measured trunk shrinkage during the validation process described above in regards to FIG. 13. Water and nutrient fluxes were not limiting roots uptake, so the system then attributed trunk shrinkage to heat stress. As the day is ending and temperature already started to drop, it is too late to react to this stress, but the system learned from this experience and will adjust its thresholds accordingly in the future.

Figure 15C:
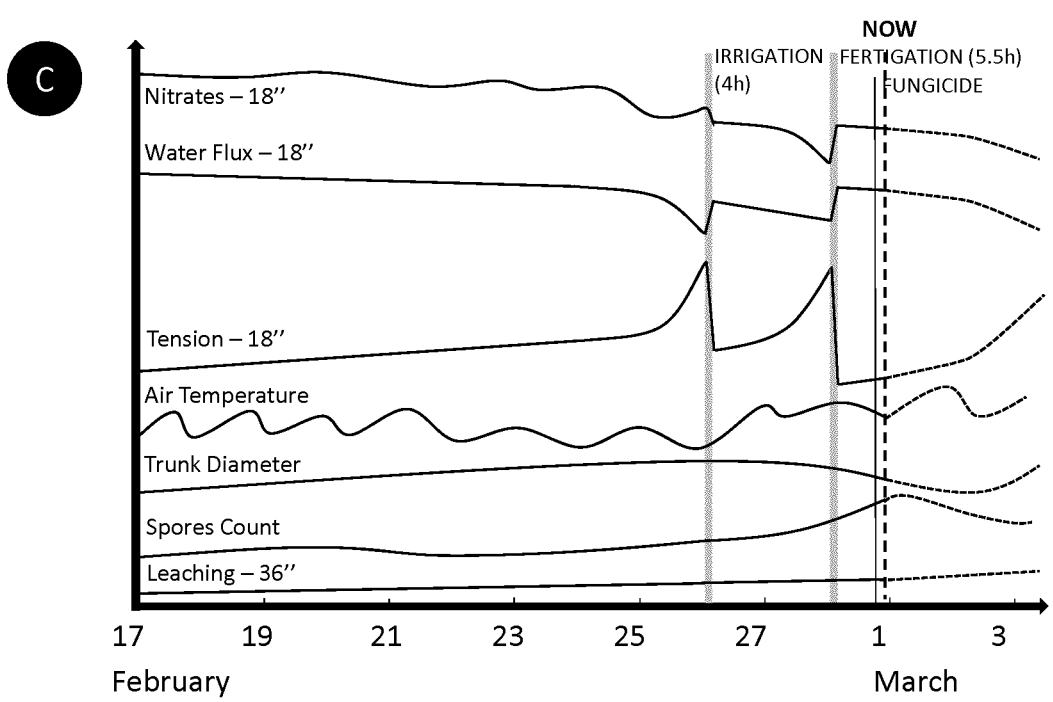

FIG. 15C illustrates the status of the system at 1:00 PM on February 29th. The current air temperature of 32° C. was not anticipated as the external weather forecast source predicted a temperature of 30° C. The air temperature in the canopy is 34° C. The system has determined, from data collected since the beginning of the flowering period, a significantly strong relationship between the number of foraging bees outside the hives and the temperature in the canopy. Bee activity is at its maximum point when canopy temperature is between 23-33° C., starts to drop linearly at 33° C., and is followed by an accelerated drop after 37° C. The system determined, by evaluating yield numbers of all other almonds fields in the past years, a yield loss of 3%/acre at harvest resulting from each day when high temperature affected bee activity linearly and 5%/acre per day after the curve drop starts accelerating. With water in the well at 6° C. and air temperature at 33° C., the system predicts water will exit micro-sprinkler heads at 19° C. and will decrease canopy temperature by 7° C. for 3 hours following a 15-minute irrigation event and which prevents the reduction in bee activity. The system is then reacting to this new condition by starting a 15-minute irrigation event after having simulated that this irrigation event will not impact negatively any other parameters or conditions of the system, and that the cost related to this irrigation event is less than the money loss associated to the yield loss.

In the 3 first years of the crop, weed removal operations were necessary at this time of the year. However, this year, with the system improving water management, a reduction of 25% in irrigation has been achieved. This results in a weed coverage still below the threshold where weed removal is profitable. The first weed removal operation of the season is not anticipated by the system before the next month. As the system still did not measure any infiltration problem, the gypsum injector has never been turned on this season. With the system taking charge of many operations, the crew of 2 workers is now enough to achieve all the manual operations on the farm. During the week of this example case study, the anticipated price for almonds at harvest did not change.

While the present technology has been described in connection with specific embodiments thereof, it will be understood that it is capable of further modifications and this application is intended to cover any variations, uses, or adaptations following, in general, the principles of the present technology and including such departures from the present disclosure as come within known or customary practice within the art to which the present technology pertains and as may be applied to the essential features hereinbefore set forth, and as follows in the scope of the appended claims.

INCORPORATION BY REFERENCE

All references cited in this specification, and their references, are incorporated by reference herein in their entirety where appropriate for teachings of additional or alternative details, features, and/or technical background.

EQUIVALENTS

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following embodiments.

What is claimed is:

1. A system for monitoring and regulating plant productivity, wherein the system is communicatively couplable to a plurality of monitoring sensors deployable in at least one crop field, wherein the system is further communicatively couplable to at least one controllable device that is operable to vary at least one production environment condition of the at least one crop field, wherein the system comprises:

at least one memory for storing a plurality of instructions, and;

at least one processor for executing the plurality of instructions to cause a method of monitoring and regulating plant productivity to be performed, the method comprising:

receiving field data from the plurality of monitoring sensors, the field data being associated with conditions of the at least one crop field sensed over a monitoring period and comprising multiple factors relating to plant productivity, the multiple factors having multiple interactions with one another;

computing a predicted value for at least one variable associated with the at least one production environment condition of the at least one crop field by inputting the field data from the plurality of monitoring sensors and at least one generated feature derived from the field data into a machine learning algorithm executed by the at least one processor, the machine learning algorithm having been trained based on a training set comprising (a) historic field data from the plurality of monitoring sensors sensed over at least a previous monitoring period, and (b) at least one generated feature derived from the historic field data, the machine learning algorithm continuously and simultaneously taking into account the interactions between the multiple factors relating to the plant productivity;

dynamically generating, based on the field data, a threshold for the at least one variable;

determining, based on the threshold associated with the at least one variable, that the predicted value for the at least one variable indicates that an intervention in the at least one crop field is to be initiated; and in response to the determining, causing the at least one controllable device to vary the at least one production environment condition.

2. The system of claim 1, wherein the method further comprises training the machine learning algorithm based on the training set.

3. The system of claim 1, wherein the method further comprises receiving data of at least one external data type, the training set further comprises at least a subset of the data of the at least one external data type, and wherein the at least one external data type comprises data from crop fields other than the at least one crop field, satellite data, drone data, environmental data, weather data, imaging and spectrography data, soil profile data, hydrological data, topographical data, data related to the crop, data related to economic variables, data associated with legal and regulatory constraints, and data associated with irrigation, scheduling constraints or cultural practices.

4. The system of claim 1, wherein the method further comprises storing data of the training set in at least one multivariate matrix.

5. The system of claim 1, wherein the method further comprises adjusting, by the at least one processor executing the machine learning algorithm, the threshold associated with the at least one variable prior to determining that the predicted value indicates that an intervention in the at least one crop field is to be initiated.

6. The system of claim 1, wherein at least some acts of the method are repeated for at least one subsequent iteration, such that for each subsequent iteration, at the receiving, the field data is associated with conditions of the at least one crop field over a respective subsequent monitoring period.

7. The system of claim 1, wherein the causing the at least one controllable device to vary the at least one production environment condition is performed automatically in response to the determining.

8. The system of claim 1, wherein the method further comprises outputting an alert that intervention in the at least one crop field is desirable, and receiving user confirmation in response to the alert prior to causing the at least one controllable device to vary the at least one production environment condition.

9. The system of claim 1, wherein the method further comprises:
generating an intervention schedule for permitting a manual assessment of whether intervention in the at least crop field is desirable; and
generating at least one performance assessment report for permitting a manual assessment of crop field performance of the at least one crop field over the monitoring period.

10. The system of claim 1, wherein the determining that the predicted value for the at least one variable indicates that intervention in the at least one crop field is to be initiated comprises: evaluating one or more values for the at least one variable that optimizes plant productivity based on at least one output parameter.

11. The system of claim 10, wherein the at least one output parameter comprises one or more of the output parameters selected from the following group: crop yield, profitability, use of water, use of energy, use of fertilizers, leaching of fertilizers, and greenhouse gas emissions.

12. The system of claim 10, wherein the at least one output parameter comprises a plurality of output parameters, wherein the method further comprises prioritizing the plurality of output parameters, and wherein the evaluating one or more values for the at least one variable that optimizes plant productivity is based on the plurality of output parameters having been prioritized.

13. The system of claim 1, wherein the method further comprises standardizing the field data, wherein the standardizing comprises aligning the field data in at least one of a spatial dimension and a temporal dimension, and wherein the predicted value for the at least one variable comprises at least one of a spatial component and a temporal component.

14. The system of claim 1, wherein the at least one generated feature derived from the field data comprises a plurality of elements computed from a decomposition of at least one time series associated with the field data.

15. The system of claim 1, wherein the causing the at least one controllable device to vary the at least one production environment condition comprises initiating a change, in the at least one crop field, in at least one of the following elements selected from the following group: water, energy, nitrogen, other elements, chemical inputs.

16. The system of claim 1, wherein the method further comprises:
taking into account a constraint corresponding to the at least one variable; and
modifying, based on the constraint, the intervention in the at least one crop field.

17. The system of claim 1, wherein the method further comprises, prior to computing the predicted value for the at least one variable, identifying, in the field data, an anomaly.

18. The system of claim 5, wherein the adjusting the threshold comprises:
determining a profit increase associated with performing an action;
determining a profit decrease associated with not performing the action; and
adjusting, based on comparing the profit increase to the profit decrease, the threshold.

19. A method of monitoring and regulating plant productivity comprising:
receiving field data from a plurality of monitoring sensors, the field data associated with conditions of the at least one crop field sensed over a monitoring period and comprising multiple factors relating to plant productivity, the multiple factors having multiple interactions with one another;
computing a predicted value for at least one variable associated with the at least one production environment condition of the at least one crop field, by inputting the field data from the plurality of monitoring sensors and at least one generated feature derived from the field data into a machine learning algorithm executed by at least one processor, the machine learning algorithm having been trained based on a training set comprising (a) historic field data from the plurality of monitoring sensors sensed over a previous monitoring period, and (b) at least one generated feature derived from the historic field data, the machine learning algorithm continuously and simultaneously taking into account the interactions between the multiple factors relating to plant productivity;
dynamically generating, based on the field data, a threshold for the at least one variable;
determining, based on the threshold associated with the at least one variable, that the predicted value for the at least one variable indicates that an intervention in the at least one crop field is to be initiated; and
in response to the determining, causing at least one controllable device to vary the at least one production environment condition.

20. A method comprising:
receiving a first set of field data from a plurality of monitoring sensors, wherein the first set of field data is associated with conditions of a crop field sensed over a monitoring period, and wherein the first set of field data comprises water tension, water content, nitrates content, and pH level;
generating at least one generated feature derived from the first set of field data;
computing, by inputting the first set of field data and the at least one generated feature into a machine learning algorithm executed by at least one processor, a predicted value for a plurality of variables associated with the crop field, the machine learning algorithm having been trained based on a training set comprising (a) historic field data from the plurality of monitoring sensors sensed over a previous monitoring period, and (b) at least one generated feature derived from the historic field data;

dynamically generating, based on the first set of field data, a threshold for each variable of the plurality of variables;

determining, based on the thresholds, a plurality of actions to be initiated in the at least one crop field;

taking into account the constraints corresponding to the plurality of actions;

modifying, based on the constraints, the plurality of actions;

establishing, for each action of the plurality of actions, a priority for each of the actions;

causing, based on the priority for each of the actions, at least one controllable device to implement a first action of the plurality of actions, wherein the first action has a highest priority of the plurality of actions;

recording, by the plurality of monitoring sensors, a second set of field data corresponding to changes that occurred due to the at least one action; and implementing, based at least in part on the second set of field data, a second action of the plurality of actions.

* * * * *